(12) United States Patent
Jagtap et al.

(10) Patent No.: US 6,534,651 B2
(45) Date of Patent: Mar. 18, 2003

(54) 7-SUBSTITUTED ISOINDOLINONE INHIBITORS OF INFLAMMATION AND REPERFUSION INJURY AND METHODS OF USE THEREOF

(75) Inventors: Prakash Jagtap, Beverly, MA (US); Garry Southan, Salem, MA (US); Andrew Salzman, Belmont, MA (US); Csaba Szabo, Gloucester, MA (US); Siya Ram, Beverly, MA (US)

(73) Assignee: Inotek Pharmaceuticals Corp., Beverly, MA (US)

( * ) Notice: Subject to any disclaimer, the term of this patent is extended or adjusted under 35 U.S.C. 154(b) by 0 days.

(21) Appl. No.: 09/766,053

(22) Filed: Jan. 19, 2001

(65) Prior Publication Data

US 2002/0095044 A1 Jul. 18, 2002

Related U.S. Application Data

(60) Provisional application No. 60/195,622, filed on Apr. 6, 2000.

(51) Int. Cl.$^7$ .................... C07D 413/12; C07D 403/12; C07D 401/12; C07D 209/46; A61P 19/02

(52) U.S. Cl. .................. 544/144; 544/544; 544/277; 544/310; 544/312; 544/373; 544/546; 544/146; 544/165; 544/200; 544/277.1; 544/548; 544/305.11; 544/312.1; 544/253; 544/467; 544/472

(58) Field of Search ................... 544/144, 277, 544/310, 312, 373; 546/146, 165, 200, 277.1; 548/305.1, 312.1, 471, 472, 473, 477, 253, 467

(56) References Cited

U.S. PATENT DOCUMENTS

| | | | |
|---|---|---|---|
| 3,855,206 A | 12/1974 | Prasad et al. | |
| 3,857,947 A | 12/1974 | Teach | |
| 3,864,483 A | 2/1975 | Stein et al. | |
| 3,914,414 A | 10/1975 | Stein et al. | |
| 3,914,415 A | 10/1975 | Stein et al. | |
| 3,966,917 A | 6/1976 | Prasad et al. | |
| 4,029,884 A | 6/1977 | Stein et al. | |
| 6,087,480 A * | 7/2000 | Lamatsch | 534/739 |
| 6,277,847 B1 * | 8/2001 | Theodoridis et al. | 514/241 |

FOREIGN PATENT DOCUMENTS

| | | |
|---|---|---|
| CA | 1019727 | 10/1977 |
| DE | 2213180 | 9/1972 |
| DE | 2417565 | 10/1974 |
| EP | 0 679 396 | 11/1995 |
| GB | 1380765 * | 1/1975 |
| WO | WO 98/54135 | 12/1998 |
| WO | WO 99/11622 | 3/1999 |
| WO | WO 99/11623 | 3/1999 |
| WO | WO 99/11624 | 3/1999 |
| WO | WO 99/11628 | 3/1999 |
| WO | WO 99/11644 | 3/1999 |
| WO | WO 99/11645 | 3/1999 |
| WO | WO 99/11649 | 3/1999 |
| WO | WO 99/36402 | 7/1999 |
| WO | WO 99/41276 A1 * | 8/1999 |
| WO | WO 99/41276 | 8/1999 |
| WO | WO 99/59973 | 11/1999 |
| WO | WO 99/59975 | 11/1999 |
| WO | WO 00/39070 | 7/2000 |
| WO | WO 00/39104 | 7/2000 |
| WO | WO 00/42040 | 7/2000 |

OTHER PUBLICATIONS

Banasik, M. et al., (1992). *J. of Bio. Chem.* 267:1569–1575.
Banasik, M. and Ueda, K. (1994). *Molecular and Cellular Biochem.* 138:185–197.
Belliotti, T. et al., (1998). *Bioorganic & Med. Chem. Letters* 8:1499–1502.
DoMinh, T. et al., (1977). *J. Org. Chem.* 42:4217–4221.
Duckworth, D. et al., (1996). *J. Chem Soc., Perkin Trans.* 1:815–821.
Dugger, H. et al., (1976). *Drug Met. and Disposition* 4:262–268.
Egbertson, M. et al., (1999). *J. Med. Chem.* 42:2409–2421.
Griffin, R. et al., (1998). *J. Med. Chem.* 41:5247–5256.
Kamochi, Y. and Watanabe, Y. (1989). *Daiichi Yakka Daigaku Kenkyu Nenpo* 20:1–10.
Kawana, M. et al., (1972). *J. Org. Chem.* 37:288–291.
Lee, J. et al., (1999). *Bioorganic & Med. Chem. Letters* 9:1365–1370.
McAlees, A. et al., (1977). *J. Chem. Soc., Perkin Trans.* 1:2038–2040.
Milam, K. and Cleaver, J. (1984). *Science* 223:589–591.

(List continued on next page.)

Primary Examiner—Mukund J. Shah
Assistant Examiner—Thomas McKenzie
(74) Attorney, Agent, or Firm—Pennie & Edmonds LLP

(57) ABSTRACT

The invention provides a novel class of substituted isoindolinone derivatives, useful for the treatment of inflammation and reperfusion injuries. Pharmaceutical compositions, and methods of making and using the compounds, or pharmaceutically acceptable salts, hydrates, stereoisomers or mixtures thereof are also described. The novel isoindolinone derivatives have the formula:

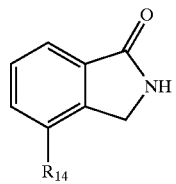

or a pharmaceutically acceptable base or acid addition salt, hydrate, stereoisomer, or mixtures thereof, wherein $R_{14}$ is described herein.

18 Claims, No Drawings

OTHER PUBLICATIONS

Norman, M. et al., (1993). *J. Med. Chem.* 36:3417–3423.
Norman, M. et al., (1994). *J. Med. Chem.* 37:2552–2563.
O'Sullivan, R. and Parkins, A. (1984). *J. Chem. Soc. Chem. Commun.* 17:1165–1166.
Prasad, R. et al., (1976). *J. Med. Chem.* 19:1180–1186.
Shinkwin, A. et al., (1999). *Bioorganic & Med. Chem.* 7:297–308.
Szabo, C. (1996). *Shock* 6:79–88.
Szabo, C. and Dawson, V. (1998). *Trends in Pharm Sci.* 19:287–298.
Tamai, H. et al., (2000). *Alcoholism: Clin. & Ex. Res.* 24:390–394.
Tomita, M. et al., (1969). *J. Chem Soc. (C)* 2:183–188.
Wang, W. et al., (1998). *J. of Surgical Res.* 79:39–46.
Wattanasirichanigoon, S. et al., (1999). *Shock* 12:127–133.
White, A. et al., (2000). *J. Med. Chem.* 43:1084–4097.
Zhang, J. et al., (2000). *Biochem. And Biophys. Res. Comm.* 278:590–598.
Babichev et al. (1970). *Chemical Abstracts* 72(25): Abstract No. 132428s.
International Search Report for PCT/US01/11288, mailed Dec. 6, 2001.
Aldrich Chemical Company, Milwaukee, WI, 1992, p. 1015.*
Handbook of Chemistry and Physics (42 Ed, Chemical Rubber Publishing, Cleveland, C.D. Hodgman, Ed.), 1960, p. 1166.*
McAlees, Alan J.; McCrindle, Robert; Sneddon, David W., J. Chem. Soc., Perkin Trans. 1 (18), 2038–40 (English) 1977.*
Babichev, F.S. et al, Chemical Abstracts, vol. 72, 132428s, 1970.*

* cited by examiner

7-SUBSTITUTED ISOINDOLINONE INHIBITORS OF INFLAMMATION AND REPERFUSION INJURY AND METHODS OF USE THEREOF

RELATED APPLICATIONS

This application claims priority to U.S. Ser. No. 60/195,622, filed Apr. 6, 2000. The contents of this application are incorporated by reference in their entirety.

STATEMENT OF GOVERNMENT SUPPORT

This invention was made with United States Government support under grant number R44NS37642-02, awarded by the National Institute of Neurological Disorders and Stroke (NINDS). The United States Government has certain rights in the invention.

FIELD OF THE INVENTION

The invention relates generally to inhibitors of inflammation and reperfusion injury. In particular, the invention relates to 2,3-dihydro-isoindol-1-one derivatives and nucleoside analogs, and more particularly to nucleoside-isoindolinone conjugates.

BACKGROUND OF THE INVENTION

Inflammation disorders, such as arthritis, colitis, and autoimmune diabetes typically manifest themselves as disorders distinct form those associated with reperfusion injury, e.g., stroke and heart attack, and can present clinically as different entities. However, there can be common underlying mechanisms between these two types of disorders. In particular, inflammation and reperfusion injury can induce proinflammatory cytokine and chemokine synthesis. Induction of pro-inflammatory cytokines can, in turn, result in production of cytotoxic free radicals such as nitric oxide (NO) and superoxide. Nitric oxide and superoxide can react to form peroxynitrite ($ONOO^-$). Szabó et al, Shock 6:79–88, 1996.

Peroxynitrite-induced cell necrosis observed in inflammation and reperfusion injury involves, in significant part, the activation of the nuclear enzyme poly (ADP-ribose) synthetase (PARS). Activation of PARS is thought to be an important step in the cell-mediated death observed in inflammation and reperfusion injury. Szabó et al., Trends Pharmacol. Sci. 19: 287–98, 1998.

A number of PARS inhibitors have been described in the art. See, e.g., Banasik et al., J. Biol. Chem., 267:1569–75, 1992, and Banasik et al., Mol. Cell. Biochem., 138:185–97, 1994. Additionally, some potent PARS inhibitors are reported in, for example, WO 00/39104, WO 00/39070, WO 99/59975, WO 99/5973, WO 99/11649, WO 99/11645, WO 99/11644, WO 99/11628, WO 99/11628, WO 99/11623, WO 99/11311, WO 00/42040; Zhang et al., Biochem. Biophys. Res. Commun., 278:590–98, 2000, White et al., J.Med. Chem., 43:4084–4097, 2000; Griffin et al., J. Med. Chem., 41:5247–5256, 1998; Shinkwin et al., Bioorg. Med. Chem., 7:297–308, 1999. Furthermore, side effects of some of the best known-PARP inhibitors have been discussed in Milan et al, Science, 223:589–591, 1984.

Certain isolindolinone derivatives are known in the art. For example, inhibitors of platelet aggregation are reported in Egbertson et al., J. Med. Chem., 42:2409–21, 1999; dopamine D4 receptor isoindolinones are reported in Belliotti et al., Bioorg. Med. Chem. Lett., 8:1499–502, 1998; antipsychotic agents are disclosed in Norman et al., J. Med. Chem., 37: 2552–63, 1994 and in Normal et al., J. Med. Chem., 36: 3417–23, 1993. The antiarrhythmic activity of isoindolione is shown in Dugger et al. Drug Metab. Dispos. 4:262–268, 1976, and substituted 2,3-dihydro-1H-isoindol-1-one derivatives for treating hyperlipemia remedy are disclosed in WO 98/54135.

Syntheses of substituted 2,3-dihydroisoindolinones, other than the compounds of the invention, are reported in, for example, Duckworth et al., J. Chem. Soc., Perkin Trans. 1:815–21, 1996; Kamochi et al., Daiichi Yakka Daigaku Kenkyu Nenpo 20:1–10, 1989; McAlees et al., J. Chem. Soc. Perkin Trans 1, 1:2038–2040, 1977; Tomita et al., J. Chem. Soc. C, 2:183–8, 1969; Do Minh et al., J. Org. Chem., 42:4217–4221, 1977; and O'Sullivan et al., J. Chem. Soc. Chem. Commun., 17:1165–1166, 1984.

Various nucleoside peptides and amide derivatives are shown in, for example, Kawana et al. , J. Org. Chem., 37:288–91 (1972); U.S. Pat. Nos. 3,864,483; 3,914,414; 3,914,415; 3,966,917; 4,029,884; and in German patents DE 2417465 and DE 2213180.

SUMMARY OF THE INVENTION

The invention is based in part on the discovery of novel compounds and their unexpected effects in inhibiting inflammation and in treating reperfusion injuries.

Accordingly, one aspect of the invention includes novel substituted isoindolinone derivatives. In another aspect, the invention relates to substituted nucleoside analogs. In yet another aspect, the invention includes a conjugate according to Formula I, as set forth in the Detailed Description of the Invention, below.

Also provided by the invention is a method of treating inflammatory and reperfusion conditions in mammals by administering to a mammal in need of such treatment an effective amount of the compounds of the invention, for example, a conjugate according to Formula I.

In a further aspect, the invention also includes a method for the production of the compounds of the invention.

In one aspect of the invention, a nucleoside or nucleoside analog is conjugated to a compound that is useful for inhibiting inflammation or for treating reperfusion injuries. In some embodiments, the nucleoside moiety increases the anti-inflammatory or anti-reperfusion activity of the conjugated compound. In a particular embodiment, a nucleoside moiety is conjugated to an isoindolinone moiety.

The compounds described in the current invention are potent compounds that can be used to treat a variety of conditions and diseases, typically those known to involve inflammatory mediator production and cell death.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

DETAILED DESCRIPTION OF THE INVENTION

The present invention provides a novel class of substituted nucleoside derivatives according to Formula I:

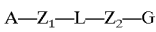

$$A—Z_1—L—Z_2—G \quad\quad I$$

or a pharmaceutically acceptable prodrug, hydrated salt, or mixtures thereof, wherein A and G are connected via $Z_1$ and $Z_2$, respectively, to a linker L.

Moiety A is a ribose-substituted mono- or bi-cyclic heterocycle accordind to formula II or III.

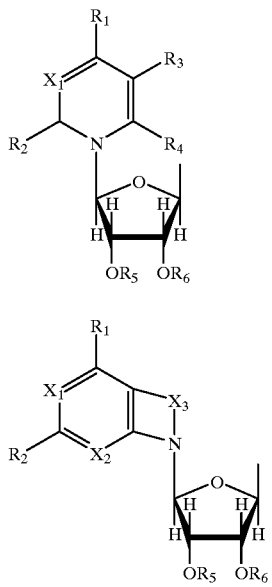

Wherein $X_1$ and $X_2$ are, independently, N or CH;

$X_3$ is $CR_7=CR_8$, $CHR_7—CHR_8$, $CR_7=N$, $N=CR_7$, $N=N$, $NR_7—O$, $CHR_7—O$ or $CHR_7—S$, where $R_7$ and $R_8$ are, independently, H, alkyl, amino, hydroxy, alkoxy;

$R_1$ and $R_2$ are, independently, H, alkyl, $NH_2$, OH, SH, Cl, $NHR_9$, $N=R_9$, $N=NR_9$, or amide, where $R_9$ is alkyl, aryl, arylalkyl, alkyl-heterocycle;

$R_3$ and $R_4$ are independently H, C1–5 alkyl, hydroxy, amino or halo;

$R_5$ and $R_6$ are, independently, alkyl, other acyl, or $R_5$ and $R_6$, taken together, form a 5-or 6-membered, substituted or unsubstituted heterocycle.

In some embodiments, A is a 5' modified purine or pyrimidine nucleoside, or a derivative thereof (e.g., where $X_1=X_2=N$, $X_3$ is $N=CH$, $R_1$ and $R_2$ are $NH_2$ or OH).

$Z_1$ is —$CH_2O$—, —$CH_2NR_{10}$—, —$CH_2NR_{10}C(O)$—, —$CONR_{10}$—, —$CO_2$—, —$CH_2NHCONH$—, —$CH_2$—, —$CH_2NHCSNH$—, —CO—, —$CH_2CO_2$—, —$NHCO_2$, S, $SO_2$, $CH_2S$, SO;

$Z_2$ is; —$NR_{10}CO$—, —$C(O)NR_{10}$—, —NHCONH—, —OC(O)—, —C(O)O—, NHCS, —CSNH—, NHCSNH, O, CO, OCO, OCONH, NH, $CH_2$, CH-alkyl, $NHCO_2$, S, $SO_2$, CS, SO.

It is understood that tautomeric forms, where possible, are included in the invention, and that where tautomerisation is possible, the tautomer represented herein as structures II or III may not represent the dominant tautomer.

The linker, L, can be H, O, S, C1–15 alkylene chain, which can be substituted in one or more positions, or a 5, 6 or 7-membered carbocycle or heterocycle (optionally substituted in one or more positions), provided that when $Z_1$ is O, L is not H, and when L is H, $Z_2$ and G are absent. In some embodiments, L is substituted with amino, alkyl, halo, hydroxy, thio, or epoxide groups in any combination;

In some embodiments, L may contain:
i) one or more heteroatoms chosen from N, O, S, alone or in any acceptable combination, including, but not limited to, $SO_2$, S—S, N=N;
ii) 5 or 6 member cyclic moieties, for example, hetercyclic, carbocyclic, aromatic or otherwise, with no restriction with respect to points of attachment to L, or to $Z_1$ or $Z_2$, where applicable. The cyclic moieties can be either unsubstituted or substituted with lower alkyl, hydroxy, keto, amino, aminoalkyl, halo, alkoxy groups. Examples of acceptable cycles include substituted aryl, substituted heterocyclic or heterocyclic amines such as piperidine, piperazine, pyrole, imidazole, benzimidazole, tetrazoles, indole, isoquinoline, quinoline, pyrrolidine;
iii) varying degrees of unsaturation, including alkene, imine, diazo; or
iv) combinations of i, ii, and iii.

In some embodiments, G can be H, OH, SH, $NH_2$, $CO_2H$, or a substituted alkyl, aryl, alkylaryl, carbocyclic, heterocyclic, bicyclic, a bicyclic heterocycle, biphenyl or heterocyclic amine such as, for example, a substituted or unsubstituted piperidine, piperazine, pyrole, imidazole, benzimidazole, tetrazole, indole, isoquinoline, quinoline, pyrrolidine.

In some aspects of the invention, G itself is an inhibitor of inflammation or of reperfusion injury. For example, G can be any inhibitor of PARS whose potency as an inhibitor of PARS is preferably increased by incorporation into a structure as indicated by Formula I. It will be recognized to those skilled in the art that the site of attachment of the linker, L, to moiety G (via $Z_2$) and the nature of L and $Z_2$, will influence the overall potency of the conjugate as an inhibitor of PARS.

In some aspects of the invention, moiety G can be a member of a novel class of isoindolone compounds represented by Formula IV, described below.

One aspect of the invention includes a compound according to Formula IV, unconjugated to the A moiety.

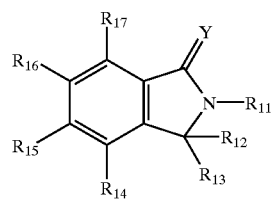

Specifically, the present invention relates to a compound of Formula IV, wherein:

Y is O, S, Se, NH, N-alkyl, or N-aryl;

$R_{11}$ is H, OH, aryl, alkyl, or an amino acid side chain;

$R_{12}$ and $R_{13}$ are, independently, a hydrogen, alkyl, aryl, heterocycle, OH, O-alkyl, O-aryl, N-alkyl, N-aryl, or, taken together, are =O, =NH, =S; and $R_{14}$, $R_{15}$, $R_{16}$, and $R_{17}$ are, independently, hydrogen, halo, alkylhalo, hydroxy, alkoxy, C1–C10 straight or branched chain alkyl, C2–C10 straight or branched chain alkenyl group, C3–C8 carbocyclic, aryl, alkylamino, amino, carboxy, ester, arylalkyl, or nitro.

In certain embodiments, $R_{14}$, $R_{15}$, $R_{16}$, and $R_{17}$ are, independently, H, $Z_2$—L—$Z_1$—A (as defined above), or Q—B—D, wherein:

Q is NHCO, NHCONH, O, CO, $OCO_2$, OCO, OCONH, NH, $CH_2$, CH-alkyl, $NHCO_2$, S, $SO_2$, CS, or SO;

B is C1–C10 straight or branched chain alkyl, C2–C 10 straight or branched chain alkenyl group, C3–C8 carbocyclic, aryl, alkylamino, amino, alkylamido, arylamido, carboxy, ester, anhydride, or an arylalkyl group substituted with one or more hydrogen, halogen, alkylhalo, hydroxy, nitro, amino, amido, carbamate, or carbonate groups; and D is hydrogen, a substituted heterocycle or carbocycle, or a straight or branched chain alkyl amine. In some embodiments, the substituents can be: hydrogen, alkylhalo, alkylhydroxy, C1–C10 straight or branched chain alkyl, C2–C10 straight or branched chain alkenyl, C2–C10 straight or branched chain alkynyl, C3–C8 carbocyclic, aryl, benzyl, alkylamino, alkylamido, alkylcarboxy, alkylester, arylalkyl, or cyclic heterocyclic amines. Substituted amines cyclic or heterocyclic amines include piperidine, piperazine, N-alkylated or alkylcarbonylated piperazines, pyrole, imidazole, benzimidazole, tetrazoles, indole, isoquinoline, quinoline, pyrrolidine, aniline, substituted aniline, purine, nucleosides, nucleotides, sugars, hydroxylated alkanes, glycerol, and other C2 to C10 branched or cyclic or cycloalkenyl amines or heterocyclic compounds.

In some embodiments, D is absent.

Also included in the invention are compounds according to Formula IV, wherein $R_{13}$ and $R_{14}$ form a heterocyclic or a carbocyclic ring containing 5 to 10 members, e.g., 5, 6, 7, 8, 9, or 10 members. Alternatively, $R_{14}$ and $R_{15}$ can be joined to form a 5 to 10 member heterocyclic or carbocyclic ring.

The invention also includes a pharmaceutical composition that includes a compound of the invention and a pharmaceutically acceptable carrier. For example, the invention includes a compound according to Formula I provided as a pharmaceutically acceptable prodrug, hydrated salt, or mixtures thereof.

Salts encompassed within the term "pharmaceutically acceptable salts" refer to non-toxic salts of the compounds of this invention which are generally prepared by reacting the free base with a suitable organic or inorganic acid to produce "pharmaceutically acceptable acid addition salts" of the compounds described herein. These compounds retain the biological effectiveness and properties of the free bases. Representative salts include, e.g., water-soluble and water-insoluble salts, such as the acetate, amsonate (4,4-diaminostilbene-2,2'-disulfonate), benzenesulfonate, benzonate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methylene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

Methods of Using Substituted Nucleoside Derivatives

The invention also includes a method of inhibiting poly (ADP)-ribose synthase activity (PARS) in a cell. This enzyme, which is also known as poly(ADP-ribose) synthetase and PARP (poly(ADP-ribose) polymerase, EC 2.4.99), and ADP-ribosyltransferase (ADPRT, EC 2.4.2.30), is a nuclear enzyme that catalyzes a transfer of the ADP ribose moiety of NAD+ to an acceptor protein.

The method includes contacting the cell with a compound of Formula I or IV in an amount sufficient to inhibit poly (ADP)-ribose-synthase in the cell. In general, any cell having, or capable of having, PARS activity, can be used. The cell can be provided in any form as long as it is accessible to the compound. For example, the cell can be provided in vitro, ex vivo, or in vivo. PARS activity can be measured using any method known in the art, e.g., methods as described in Banasik et al, *J. Biol. Chem.* 267:1569–75 (1991).

Also provided in the invention is a method of inhibiting, preventing, or treating inflammation in a subject. The inflammation can be associated, e.g., with an inflammatory disease. Inflammatory diseases refer to diseases or conditions where there is an inflammation of the body tissue. These include local inflammatory responses and systemic inflammation. Examples of such diseases and conditions include: transplant rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gum, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases including diabetes mellitus, immune-complex vasculitis, systemic lupus erythematosus (SLE); and inflammatory diseases of the heart such as cardiomyopathy, ischemic heart disease hypercholesterolemia, atherosclerosis; as well as various other diseases with significant inflammatory components, including preeclampsia; chronic liver failure; brain and spinal cord trauma, and cancer. There may also be a systemic inflammation of the body, exemplified by gram-positive or gram negative shock, hemorrhagic or anaphylactic shock, or shock induced by cancer chemotherapy, e.g., shock associated with pro-inflammatory cytokines.

The invention also includes a method of treating, preventing, or otherwise inhibiting reperfusion injury in a subject in need of treatment, prevention, or inhibition thereof. The method includes administering a compound of the invention in an amount sufficient to inhibit reperfusion injury in the subject. Reperfusion refers to the process whereby blood flow in the blood vessels is resumed after blood flow has been interrupted, such as occurs following constriction or obstruction of the vessel. Reperfusion is typically associated with ischemia and may result following a naturally occurring episode, such as a myocardial infarction or stroke, or during a surgical procedure where blood flow in vessels is purposely or unintentionally blocked off.

The subject in the above-mentioned methods can be, e.g., a mammal, e.g., a human, mouse, rat, dog, cat, horse, cow, pig, or non-human primate. Administration can be systemic or topical, and can be prophylactic or therapeutic.

The term "pharmacologically effective amount" means that amount of a drug or pharmaceutical agent that will elicit the biological or medical response of a tissue, system, animal or human that is being sought by a researcher or clinician.

The invention also includes pharmaceutical compositions suitable for inhibiting or preventing inflammation or reperfusion injury, PARS activity, or more than one of these activities. In practice, the compounds or their pharmaceutically acceptable salts, are administered in amounts which will be sufficient to inhibit inflammatory conditions or disease and/or prevent the development of inflammation or inflammatory disease in a subject, such as a mammal, and are used in the form most suitable for such purposes. The compositions are preferably suitable for internal use and include an effective amount of a pharmacologically active compound of the invention, alone or in combination, with one or more pharmaceutically acceptable carriers. The compounds are especially useful in that they have very low, if any toxicity.

The compounds herein described can form the active ingredient of a pharmaceutical composition, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like. The compositions typically will include an effective amount of active compound or the pharmaceutically acceptable salt thereof, and in addition, and may also include any carrier materials as are customarily used in the pharmaceutical sciences. Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages.

Administration of the active compounds and salts described herein can be via any of the accepted modes of administration for therapeutic agents. These methods include systemic or local administration such as oral, nasal, parenteral, transdermal, subcutaneous, or topical administration modes.

For instance, for oral administration in the form of a tablet or capsule (e.g., a gelatin capsule), the active drug component can be combined with an oral, non-toxic pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The compounds of the invention can also be administered in such oral dosage forms as timed release and sustained release tablets or capsules, pills, powders, granules, elixirs, tinctures, suspensions, syrups and emulsions.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parental injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the compounds of the present invention range from 0.002 mg to 50 mg per kg of body weight per day.

Compounds of the present invention may be administered in a single daily dose, or the total daily dosage may be administered in divided doses of two, three or four times daily.

Any of the above pharmaceutical compositions may contain 0.1–99%, 1–70%, or, preferably, 1–50% of the active compounds of the invention as active ingredients.

Methods of Making the Compounds of the Invention

Examples of synthetic pathways for making compounds according to the invention are set forth in the Examples below. For example to prepare isoindolinone compounds according to Formula IV, 3-nitro, 3-fluoro, 3-hydroxy or 3-ethylcarbonate substituted esters are prepared by standard esterification methods (e.g., SOCl$_2$/alcohol and alcohol/acid) and treated with NBS to make corresponding 2-bromomethylene benzoate derivatives. The 4-substituted isoindolinones are prepared by reacting a methanolic solution of ammonia with a corresponding 2-bromomethylene benzoic acid esters. The 4-nitroisoindolinones are reduced to 4-amino isoindolinones by a hydrogenation reaction, and then treated with various acid chlorides, anhydrides or isocyanates to generate amide and carbamate derivatives. The 4-N-chloroacetyl and other C-4 substituted derivatives can be treated with various amines, acid chlorides or other electrophiles to yield compounds according to Formula IV.

The 4-aminoisoindolinone acid derivatives (compounds 54–64) are treated with 2',3'-isopropylidene-5'-aminomethyl adenosine in presence of 1-(3-dimethylaminopropyl)-3-ethylcarbodiimide hydrochloride (EDCI) to generate adenosine amide derivatives, and then the protected adenosine amides are deprotected using TFA and water to yield compounds according to Formula IV (compounds 101–108 and 111–120). Lee et al., Bioorg. & Med. Chem. Lett., 9:1365–1370, 1999. The 4-amino derivatives (compounds 65–74) are treated with 2',3'-isopropylidene-adenosine-5'-carboxylic acid in presence of 1-(3-dimethylaminopropyl)-3-ethylcarbodiimide hydrochloride (EDCI) or dicyclohexylcarbodiimide (DCC) to generate 2',3'-isopropylideneadenosine amide derivatives, and then the isopropylidene group is deprotected using TFA and water to yield compounds according to Formula IV (compounds 123–130) and 111–120). Kawana et al., J. Org. Chem. 37:288–291, 1972.

It is to be understood that while the invention has been described in conjunction with the detailed description thereof, the foregoing description is intended to illustrate and not limit the scope of the invention. The invention will be further described in the following examples, which do not limit the scope of the invention described in the claims. The following examples illustrate the synthesis of novel compounds of the invention, and of the use of these compounds to inhibit inflammation and reperfusion.

EXAMPLES

Example 1

Synthesis of Substituted 2,3-dihydro-isoindol-1-ones a) General Methods $^1$NMR spectra were obtained from Varian 300 MHz spectrophotometer and chemical shift is reported in parts per million (ppm, δ). TLC was carried out on precoated TLC plates with silica gel 60 F-254 and preparative TLC on precoated Whatman 60A TLC plates. All intermediates and final compounds were characterized on the basis of $^1$NMR and mass spectrometry (MS) data. An exemplary synthesis of a nucleoside-isoindolinone conjugate is outlined in Scheme 1.

Scheme I

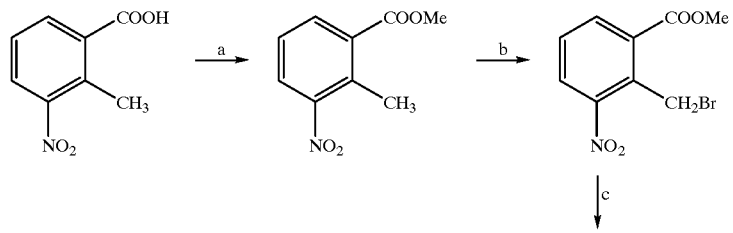

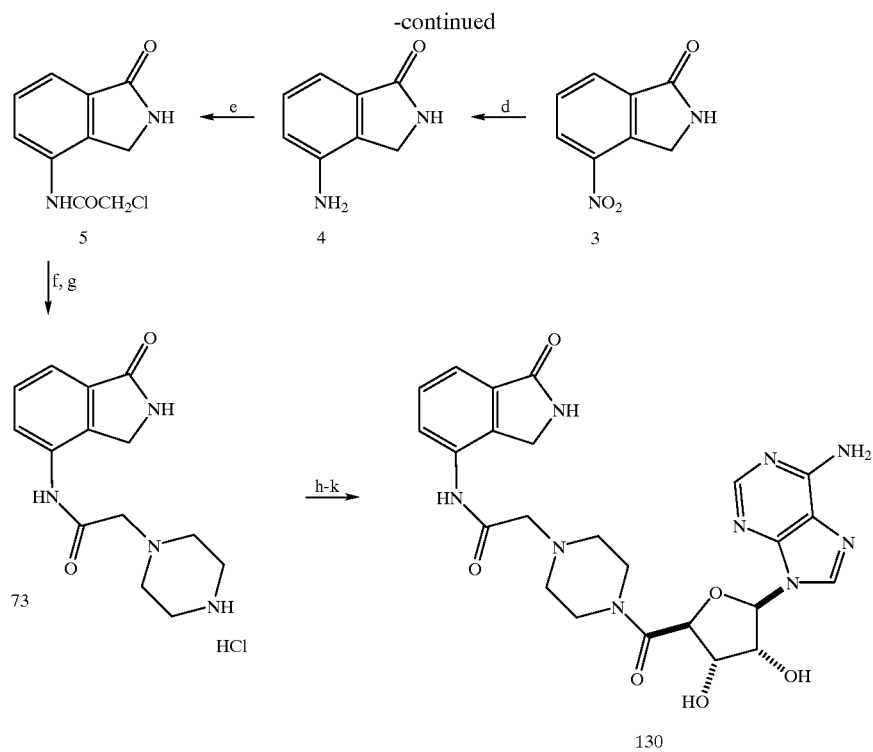

Reagents:
a. CH₃OH, H₂SO₄; b. NBS, CHCl₃ or CH₂Cl₂, AIBN; c. NH₃——CH₃OH;
d. Ammonium formate, Pd-C, CH₃OH or CH₃OH——DMF;
e. EtOAc, Sat. NaHCO₃, ClCOCH₂Cl; f. t-BOC——piperazine, CH₃OH; g. HCl——Dioxane, CH₃OH;
h. Adenosine-2′, 3′-isopropylidene-5′-carboxylicacid, DCC(or EDCl), Pr₂NEt, CH₃CN(or DMF/CH₂Cl₂);
i. TFA, water; j. NH₃——CH₃OH; k. HCl——Dioxane, CH₃OH.

b) Synthesis of methyl-2-bromomethyl-3-nitro-benzoate:

To a well stirred solution of methyl-4-nitro-2-methyl-benzoate (5 gm, 0.025 mol.) in carbon tetrachloride or CH₂Cl₂ (75 ml) was added N-bromo-succinimide (NBS) (4.950 gm, 0.03 mol) and AIBN (50 mg) and the homogeneous reaction mixture was refluxed for 16 hr or until the starting material had completely reacted. The reaction mixture was then cooled to room temperature, and the succinimide was removed by filtration. The filtrate was concentrated to give crude product, which after treatment with hexane provided methyl-2-bromomethyl-3-nitro-benzoate as a white solid (6.9 gm, 98% yield).

c) Synthesis of 4-nitro-2,3-dihydro-1H-isoindol-1-one (3):

To a solution of methyl-2-bromomethyl-3-nitro-benzoate (6.9 gm, 0.025 mol.) in methanol, was added slowly a methanolic solution of ammonia (50 ml), and the reaction mixture was stirred at room temperature for 2 hr. The pale yellow colored solid separated out was filtered, dried under vacuum to give 4-nitro-2,3-dihydro-1H-isoindol-1-one (compound 3, 3.570 gm, 81%).

¹HNMR (DMSO-D₆): 4.73 (s, 2H), 7.66 (dd, 1H), 8.03 (d, 1H), 8.32 (d, 1H), 8.8 (bs, 1H).

d) Synthesis of 4-amino-2,3-dihydro-1H-isoindol-1-one (4):

To a solution of 4-nitro-2,3-dihydro-1H-isoindol-1-one (compound 3, 3.2 gm, 0.018 mmol.) in DMF (10 ml), was added ammonium formate (5.750 gm), and Pd—C (100 mg), and the reaction mixture was stirred at 100° C. for 30 min. The mixture was then filtered through a pad of celite, and the celite was washed with DMF (10 ml) and water (10 ml). The filtrate was concentrated under vacuum to give compound 4 (2.2 gm, 83%).

¹NMR (DMSO-D₆): 4.20 (s, 2H, CH₂), 5.20 (bs, NH₂), 6.82 (dd,1H, Ar—H), 7.02 (dd,1H, Ar—H), 7.16 (t,1H, Ar—H), 8.20 (bs,1H).

e) General Synthesis of 2,3-dihydro-1H-isoindol-1-ones (5, 76, and 77) from compound 3:

To a solution compound 3 (3.250 gm, 0.018 mmol.) in DMF (20 ml), was added ammonium formate (5.750 gm), and Pd—C (100 mg), and the reaction mixture was stirred at 100° C. for 30 min. The mixture was then filtered through a pad of celite, and the celite was washed with DMF (10 ml) and water (10 ml). The filtrate was transferred into a 250 ml round bottom flask along with 10 ml ethyl acetate, and treated with an aqueous NaHCO₃ solution, followed by the addition of excess chloroacetyl chloride at room temperature. The reaction mixture was stirred at room temperature (RT) for 30 min. A solution of saturated KHCO₃ was then added and the resultant solid was filtered and dried under vacuum to give 3-N-chloroacetyl-2,3-dihydro-1H-isoindol-1-one, 5 (3.2 gm, 80%). Using similar methods, chloropropanyl, and chlorobutanyl derivatives were synthesized.

f) Synthesis of 4-N,N-dialkylacetamido-2,3-dihydro-1H-isoindol-1-ones (6–8, 11–24, and 68–72):

To a solution of 4-chloroacetyl-2,3-dihydro-1H-isoindol-1-one 6 (0.5 gm) in DMF or CH₃OH (5 ml) a solution of amine in methanol or DMF (5 ml) was added, and the reaction mixture was stirred at room temperature for 2–24 hr. The reaction mixture was dried under vacuum and the resultant solid was filtered, and then recrystalized from CH$_3$OH-ether to give 4-aminocompounds. The HCl salt of isoindolinone 7 was prepared using a solution of HCl in ether (2 M, 10 ml) and CH$_3$OH. The resulting solid was filtered and washed thoroughly with dry ether, and recrystalized from methanol-ether.

g) Synthesis of 4-N-(N-methylpiperazine)propylamido-2,3-dihydro-1H-isoindol-1-one (9):

To a solution of 4-chloropropanyl-2,3-dihydro-1H-isoindol-1-one (compound 76, 0.140 gm, 0.58 mmol) in CH$_3$OH (1 ml) a solution of N-methyl piperazine (5 ml) was added and the reaction mixture was stirred at room temperature for 1 hr. A solid formed and was separated by filtration, then washed thoroughly with dry ether, and recrystalized from methanol-ether to provide compound 9 (0.110 gm, 62%).

h) Synthesis of 4-N-(N-methylpiperazine)butylamido-2,3-dihydro-1H-isoindol-1-one (10):

To a solution of 4-chlorobutyryl-2,3-dihydro-1H-isoindol-1-one (Compound 77, 0.100 gm, 0.39 mmol) in CH$_3$OH (1 ml) a solution of N-methyl piperazine (5 ml) was added and the reaction mixture was stirred at room temperature for 1 hr. The precipitate was filtered and washed thoroughly with dry ether, and recrystalized from methanol-ether to provide 10 (0.045 gm, 36%).

i) Synthesis of 3-methylcarbonate-2-bromomethyl-methylbenzoate:

To a solution of 3-hydroxy-2-methyl-methylbenzoate (4.7 gm, 0.028 mol) and pyridine (5 ml) in methylene chloride (100 ml), a solution of methylchloroformate (1.5 eq) was added at 0° C., and the reaction mixture was stirred at room temperature for 1 hr. The reaction mixture was then poured on ice and extracted with methylene chloride. After the usual workup, the resulting residue was used for the next reaction.

To a solution of the above compound (0.380 gm, 0.0016 mol.) in CCl$_4$ (10 ml), NBS was added (0.450 gm, 0.0025 mol.) and the reaction mixture was refluxed until the starting material was completely gone, as evidenced by thin layer chromatography. The succinimide was filtered, and the filtrate was washed with water, dried over Na$_2$SO$_4$ and concentrated under vacuum. The residue was recrystalized from ethyl acetate hexane to give 3-methylcarbonate-2-bromomethyl-methylbenzoate (0.415 gm, 85%).

j) Synthesis of 4-hydroxy-2,3-dihydro-1H-isoindol-1-one (27):

To a solution of 3-methylcarbonate-2-bromomethyl-methylbenzoate (0.200 gm, 0.65 mmol) in methanol (5 ml) a methanolic ammonia solution (10 ml) was added, and the reaction mixture was stirred at room temperature for 2hr. Then the reaction mixture was poured on ice and extracted with ethyl acetate (2×15 ml). After the standard workup the resulting solid was recrystalized in methanol to give compound 27 (0.085 gm, 86%).

1HNMR (DMSO-D6): 4.20 (s, 2H), 6.94 (d, 1H), 7.09 (d, 1H), 7.26 (t, 1H), 8.45 (s, 1H), 9.96 (s, 1 H).

k) Synthesis of 2,3-dihydro-1H-isoindol-1-one (29):

To a solution of 4-hydroxy 2,3-dihydro-1H-isoindol-1-one (27) (0.250 gm, 1.67 mmol) in DMF (5 ml) K$_2$CO$_3$ and was added, followed by addition of methyl bromoacetate, and the reaction mixture was stirred at room temperature for 2hr. Then the reaction mixture was then poured on ice and extracted with ethyl acetate (2×15 ml). After the standard workup, the residue was dissolved in methanol (3 ml), and treated with NaOH (5 ml, 1N) at 0° C. and then stirred for and additional hour. After the standard workup, the solid was recrystalized in methanol to give compound 29 (0.140 gm, 60%).

l) Synthesis of isoindolinone (25):

The suspension of 2,3-dihydro-1H-isoindol-1-one 4 (0.100 gm, 0.61 mmol.) in ethyl acetate and aq. NaHCO$_3$ solution, was added m-nitrobenzoyl chloride (0.15 mg, 0.81 mmol.) at room temperature. The reaction mixture was stirred at room temperature for 30 min, and solid separated was filtered and dried under vacuum to give 2,3-dihydro-1H-isoindol-1-one 25 (0.041 gm, 36%).

m) Synthesis of 2,3-dihydro-1H-isoindol-1-one (32):

To a solution of 4-hydroxy isoindolinone 27 (0.100 gm, 0.67 mmol) in methylene chloride (5 ml) and triethylamine (0.2 ml), was added m-nitrobenzoyl chloride (0.125 gm, 0.67 mmol) at 0° C., and the reaction mixture was stirred at room temperature for 5 hr. After the usual workup, the resulting residue was purified by PTLC plate (solvent was 10% methanol-methylene chloride) to give 2,3-dihydro-1H-isoindol-1-one 32 (0.025 mg, 28%).

n) Synthesis of 4-aminomethylene-2,3-dihydro-1H-isoindol-1-one (33):

To a solution of methyl-2,3-dibromomethylene-benzoate (0.500 gm, 0.0015 mol.) in methanol (5 ml), was added methanolic ammonia solution (10 ml), and the reaction mixture was concentrated. The residue obtained was dissolved in water (5 ml) and extracted with ethyl acetate. The aqueous fraction was concentrated under vacuum to give compound 33 (0.235 gm, 94%).

o) Preparation of 4-N-(succinyl)-2,3-dihydro-1H-isoindol-1-one (55):

A mixture of 4-aminoisoindol-1-one (0.26 gm, 1.8 mmol.) and succinic anhydride (0.192 gm, 1.9 mmol.) in anhydrous CHCl$_3$ (10 ml) was refluxed for 2.5 h, and the reaction mixture was left at room temperature for 12 h. Then, the solvent was removed under reduced pressure and the residue was triturated with anhydrous ether. A white colored solid separated out, which was filtered, washed with anhydrous ether and dried under vacuum. Yield 0.36 g (82%).

$^1$HNMR(CDCl$_3$+a few drops of DMSO-D$_6$): 2.54 (bt, 2H, CH$_2$), 2.64 (bt, 2H, CH$_2$), 4.30 (s, 2H, CH$_2$) 7.35–7.55 (m, 2H, Ar—H), 7.70–7.90 (m, 1H, Ar—H), 8.52 (s,1H, exchangeable with D$_2$O), 9.88 (s,1H, NHCO, exchangeable with D$_2$O).

A reaction of variety of anhydrides can be used, such as, for example, glutaric anhydride (to produce compound 56) or maleic anhydride (to produce compound 35).

p) A General Procedure for the Preparation of 4-N-(diamido)-2,3-dihydro-1H-isoindol-1-one derivatives (49–51):

A suspension of the appropriate 4-isoindolin-1-one acid (390 μmol) and EDAC-HCl (396 μmol) in dichloromethane (3 ml) was stirred for 10 min. Then, diisopropylethylamine (80 μl) and a solution of the appropriate amine (382 μmol) in DMF (0.5 ml) were added. The resulting reaction mixture was stirred at room temperature for 24 h to 72 h. Progress of the reaction was monitored by TLC. After completion, the reaction solvent was removed under reduced pressure and the crude product was purified by prep TLC or by crystallization. A variety of alkyl or aryl amines were reacted with isoindolin-1-one acid to produce the corresponding derivatives, compounds 49–51.

q) Preparation of 4-N-(tetrahydroisoquinolino-succinamido)-2,3-dihydro-1H-isoindol-1-one (36):

A mixture of tetrahydroisoquinoline (2.65 ml, 8 mmol) and succinic anhydride (2.06 gm, 20.6 mmol) in anhydrous CHCl$_3$ (40 ml) was refluxed for 2.5 h. Then, the reaction mixture was cooled and diluted with dichloromethane (200 ml). The organic layer was washed with citric acid, water and brine and dried over sodium sulfate. The organic layer, on evaporation gave the tetrahydroisoquinolinosuccinic acid derivative. A small amount of the above acid (0.162 gm, 7 mmol) was dissolved in an anhydrous dichloromethane:THF mixture (6 ml, 3/3). To this solution EDAC-HCl (0.134 gm, 7 mmol), diisopropylethylamine (0.17 ml, 9.8 mmol) and a solution of 4-aminoisoindol-1-one (0.094 gm, 6.4 mmol) in DMF (0.3 ml) were added, respectively. The resulting reaction mixture was stirred at room temperature for 120 h. After completion, solvent was removed under reduced pressure and the residue was triturated with NaHCO$_3$ solution. A solid separated out, which was filtered, washed with water, 1N HCl, water and dried under vacuum. Yield 0.175 g (70%).

$^1$HNMR(DMSO-D$_6$): 2.60–3.00 (m, 6H, CH$_2$), 3.30–3.80 (m, 2H, CH$_2$), 4.30 (s, 2H, CH$_2$) 4.68 (d, 2H, CH$_2$), 7.05–7.15 (m, 4H, Ar—H), 7.35–7.45 (m, 2H, Ar—H), 7.87 (m, 1H, Ar—H), 8.50 (s,1H, exchangeable with D$_2$O), 9.78 (s,1H, NHCO, exchangeable with D$_2$O).

r) Preparation of 4-N-(arginyl)-2,3-dihydro-1H-isoindol-1-one (42):

To a solution of Boc-Arg (BOC)$_2$—OH (0.334 gm, 700 μmol) in THF (4 ml), EDAC-HCl (0.136 gm, 710 μmol) was added and resulting reaction mixture was stirred at room temperature for 10–15 min. Then, diisopropylethylamine (0.2 ml, 1140 μmol ) and a solution of 4-aminoisoindol-1-one (0.1 gm, 668 μmol) in DMF (1 ml) were added, respectively. The resulting reaction mixture was stirred at room temperature for 5 days. Then the solvent was removed under reduced pressure and product was extracted with ethyl acetate. The organic layer was washed with NaHCO$_3$, brine, dried over sodium sulfate, and evaporated under reduced pressure. The residue was treated with 4N HCl-dioxane (2 ml) and the resulting mixture was stirred at room temperature for 4 h. After completion, solvent was removed under vacuum, and residue was triturated with ether. A solid had separated, which was filtered and dried under vacuum. Yield 94 mg (34%).

$^1$HNMR(DMSO-d$_6$+D$_2$O): 1.40–1.65 (m, 2H, CH$_2$), 1.80–2.00 (m, 2H, CH$_2$), 3.05–3.35 (s, 2H, CH$_2$), 4.08 (t, 1H, CH), 4.40 (s, 2H, CH$_2$), 7.45–7.65 (m, 2H, Ar—H), 7.82 (d, 1H, Ar—H).

By using this approach, a number of amino acid derivatives of 4-aminoisoindolin-1-one were prepared.

s) Preparation of 1-N-{4-(2,3-dihydro-1H-isoindol-1-one)}-3-N-alkyl/aryl-ureas (46 and 47):

To a solution of 4-amino-2,3-dihydro-1H-isoindol-1-one 4 (222 μmol) in anhydrous DMF (0.5 ml), a solution of an appropriate alkyl or aryl isocyanate (224 μmol) in dichloromethane was added. The resulting reaction mixture was stirred at room temperature for 48 h. A white solid separated during the reaction, which was filtered and washed with dichloromethane. The product was dried under vacuum, and characterized by NMR and mass spectrometry (MS) data.

1-N-isoindolinyl-3-alkyl/aryl-urea 47 was also prepared by this procedure.

t) Preparation of 2,3-dihydro-1H-isoindol-1-one (72):

To a suspension of compound 5 (41.6 gm, 0.18 mol) in CH$_3$OH (350 ml), tert-butyl piperazine carbonate (40 gm, 0.21 mol) was added and stirred further at 50° C. for 48 hr. The TLC of the reaction mixture showed completion of the reaction. Then methanol was removed under vacuum. When approximately 100 ml of methanol remained, a white solid precipitated, which was filtered and washed with cold methanol and dried under vacuum to give compound 72 (40.2 gm).

u) Preparation of 2,3-Dihydro-1H-isoindol-1-one (73):

To a well stirred suspension of 72 (10.1 gm) in CH$_3$OH (30 ml), an excess solution of HCl in dioxane (10 ml) was added at 0° C. The reaction mixture became clear after the addition of the HCl solution, and was left at room temperature for 16 hr. The white precipitate of the HCl salt had separated out, and was diluted with ethyl acetate (10 ml), filtered and washed with cold methanol and dried under vacuum to give compound 73 (9.2 gm).

v) Synthesis of isoindolinone (59):

A suspension of 2,3-dihydro-1H-isoindol-1-one 4 (7 gm, 0.04 mol.) in ethyl acetate and aq. NaHCO$_3$ solution, was treated with mono-methyloctadioic acid chloride at room temperature. The reaction mixture was stirred at room temperature for 30 min. The solid that separated was filtered and dried under vacuum to give 2,3-dihydro-1H-isoindol-1-one 85, which was hydrolyzed by KOH (5 eq) in ethanol at 0° C. to generate acid 59 (5.775 gm).

w) Preparation of 2,3-Dihydro-1H-isoindol-1-one (106):

To a well-stirred suspension of 2',3'-isopropylidene 5'-aminomethyleneadenosine (0.7 gm, 0.002 mol), EDAC (468 mg, 0.002 mol) in DMF (0.5 ml) and CH$_2$Cl$_2$ (5 ml), compound 59 (0.7 gm, 0.002 mol) was added, followed by addition of diisopropyl ethylamine (0.7 ml) at room temperature. The reaction mixture became clear after the addition of diisopropyl ethylamine, and urea started precipitating after some time. The reaction was stirred further at room temperature for 24 hrs. The residue was purified on a silica gel column using 8% CH$_3$OH—CH$_2$Cl$_2$ to give a protected derivative of compound 106. Water (0.5 ml) was added to a solution of the protected compound (0.9 gm) in TFA (5 ml) and stirred at room temperature for 30 min. The reaction mixture was concentrated under vacuum (50° C.) to remove the TFA and water. The residue was washed with ether and ethyl acetate, and recrystalized from methanol-ethyl acetate to give the TFA salt of 106 (0.575 gm).

x) Preparation of 2,3-Dihydro-1H-isoindol-1-one (130):

Compound 73 (32 gm, 0.1 mol) was added to a well stirred suspension of 2',3'-isopropylidene adenosine-5'-carboxylic acid (36.5 gm, 0.11 mol), DCC (24.5 gm, 0.118 mol), N-hydroxy-succinimide (11.87 gm, 0.11 mol) in DMF (200 ml), and was followed by the addition of diisopropyl ethylamine (40 ml, 0.22 mol) at room temperature. The reaction mixture became clear after the addition of diisopropyl ethylamine, and urea started precipitating after some time. The reaction was left at room temperature for 3 days. The white precipitate of urea was filtered and washed thoroughly with DMF. The filtrate was concentrated under vacuum to remove diisopropyl ethylamine, and then treated with acetic acid (2 eq.) to break the DCC complex. Again, the solid was filtered and discarded. The filtrate was concentrated under high vacuum at 60° C., and the residue was purified on the silica gel column using 8% CH$_3$OH—CH$_2$Cl$_2$ to give a of 2',3'-isopropylidene adenosine protected derivative of compound 130.

To a solution of the protected derivative of compound 130 (3.540 gm) in TFA (15 ml) was added water (0.4 ml) and the mixture was stirred at room temperature for 1.5 hr. The reaction mixture was concentrated under vacuum (50° C.) to remove TFA and water. The residue was washed with ether and ethyl acetate, and recrystalized from methanol-ethyl acetate to give the TFA salt of 130 (3.495 gm), which was neutralized using a solution of ammonia in methanol (7N) at 0° C., and stirred at room temperature for 10 min. Next, the reaction was diluted with ethyl acetate or ether (10 ml) and the solid was filtered, washed thoroughly with ethyl acetate or ether and dried under vacuum to yield the free base of compound 130. See Scheme 1.

To a suspension of the free base (2.605 gm) in methanol (10 ml), was added a solution of HCl in dioxane (4M, 4 ml) and stirred at room temperature for 45 min. Then, it was diluted with ether or ethyl acetate (10 ml) and the solid was filtered, washed thoroughly with ether, recrystalized from $CH_3OH$, and dried under vacuum to furnish the HCl salt of 130 (2.500 gm).

Example 2

Effects of substituted 2,3-dihydro-isoindol-1-ones on in vitro inflammation models:

In in vitro studies, J774 macrophages were exposed to peroxynitrite to induce activation of PARS and related cell injury. When the macrophages were treated with the compounds listed in Table 1, below, the compounds inhibited the activation of PARS and protected against the associated cell necrosis. The results for various substituted isoindolinones are shown in Table 1.

TABLE 1

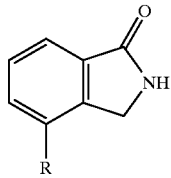

| Cmpd No. | R | % Inhibition (10 μM) |
|---|---|---|
| 1 | H | 33 |
| 2 | F | 27 |
| 3 | $NO_2$ | 12 |
| 4 | $NH_2$ | 27 |
| 5 | $NHCOCH_2Cl$ | 29 |
| 6 | $NHCOCH_2N(CH_3)_2$ | 66 |
| 7 | $NHCOCH_2N(CH_2CH_3)_2$ | 74 |
| 8 | $NHCOCH_2$-4-N-methylpiperazine | 66 |
| 9 | $NHCOCH_2CH_2$—N-methylpiperazine | 59 |
| 10 | $NHCOCH_2CH_2CH_2$—N-methylpiperazine | 35 |
| 11 | $NHCOCH_2NHCH_2CH_3$ | 66 |
| 12 | $NHCOCH_2$-piperidine | 66 |
| 13 | $NHCOCH_2$-1,2,3,4-tetrahydroisoquinoline | 80 |
| 14 | $NHCOCH_2N(CH_3)CH_2Ph$ | 56 |
| 15 | $NHCOCH_2$-(S)-prolinol | 83 |
| 16 | $NHCOCH_2$-(9-adenine) | 71 |
| 17 | $NHCOCH_2$-9-(6-chloropurine) | 75 |
| 18 | $NHCOCH_2$-9-(6-N,N-dimethylaminpurine) | 79 |
| 19 | $NHCOCH_2$-benzimidazole | 61 |
| 20 | $NHCOCH_2$-ethylnipecotate | 58 |
| 21 | $NHCOCH_2$-morpholine | 56 |
| 22 | $NHCOCH_2$-pyrrolidine | 51 |
| 23 | $NHCOCH_2$-1,2,3,4-tetrahydro-6,7-$(OCH_3)_2$-isoquinoline | 72 |
| 24 | $NHCOCH_2$-4-indolemethyl ester | 78 |
| 25 | NHCO-m-$NO_2$-benzoyl | 78 |
| 26 | $NHCOCH_2CH_2COOC(NH$-cyclohexyl$)_2$ | 49 |
| 27 | OH | 60 |
| 28 | $OCH_3$ | 64 |
| 29 | $OCH_2COOCH_3$ | 56 |
| 30 | $OCH_2COOH$ | 45 |

TABLE 1-continued

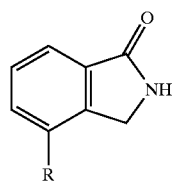

| Cmpd No. | R | % Inhibition (10 μM) |
|---|---|---|
| 31 | $OCH_2CO$-1,2,3,4-tetrahydroisoquinoline | 80 |
| 32 | OCO-m-$NO_2$benzoyl | 66 |
| 33 | $CH_2NH_2$ | 64 |
| 34 | $CH_2NHCO$-m-$NO_2$-benzoyl | 45 |
| 35 | NHCOCH=CHCOOH | 20 |
| 36 | $NHCO(CH_2)_2$—CO-1,2,3,4-tetrahydroisoquinoline | 64 |
| 37 | $NHCO(CH_2)_3$—CO-1,2,3,4-tetrahydroisoquinoline | 63 |
| 38 | $NHCONH(CH_2)_3$—OH | 58 |
| 39 | NHCONH-cyclohexyl | 37 |
| 40 | $NHCO(CH_2)_4$—$NH_2$ | 55 |
| 41 | $NHCOCHNH^tBoc$-$(CH_2)_3$—NH—C=NHNtBoc | 42 |
| 42 | $NHCOCHNH_2$—$(CH_2)_3$-guanidine | 72 |
| 43 | $NHCOCHNH^tBoc(5-CH_2$—N-$^t$Boc-imidazole) | 41 |
| 44 | $NHCOCHNH^tBoc(3-CH_2$-indole) | 47 |
| 45 | $NHCOCHNH_2(3-CH_2$-indole) | 60 |
| 46 | NH-prolinyl | 46 |
| 47 | NH-nipecotyl | 68 |
| 48 | NH-3,4,5-$(OCH_3)_3$-benzoyl | 37 |
| 49 | $NHCOCH_2CH_2CONH(2-CH_2$-benzimidazole) | 43 |
| 50 | $NHCO(CH_2)_2$—CO—$NH(CH_2)2$-piperidine | 42 |
| 51 | $NHCO(CH_2)_2$—CO—$NH(CH_2)_2$-2-pyridine | 45 |
| 52 | $NHCOCH(NHCOOC_7H_7)(CH_2)_4NHBoc$ | 14 |
| 53 | $NHCOCH(NHCOOC_7H_7)(CH_2)_4NH_2$ | 46 |
| 54 | $NHCOCH_2COOH$ | NT (not tested) |
| 55 | $NHCO(CH_2)_2COOH$ | 25 |
| 56 | $NHCO(CH_2)_3COOH$ | 32 |
| 57 | $NHCO(CH_2)_4COOH$ | NT |
| 58 | $NHCO(CH_2)_5COOH$ | NT |
| 59 | $NHCO(CH_2)_6COOH$ | NT |
| 60A | $NHCO(CH2)_7COOH$ | NT |
| 60B | $NHCO(CH_2)_8COOH$ | NT |
| 61 | $NHCO(CHOAc)_2COOH$ | NT |
| 62 | $NHCO(CF_2)_3COOH$ | NT |
| 63 | $NHCONHCH_2COOH$ | NT |
| 64 | $NHCOCH_2OCH_2COOH$ | NT |
| 65 | $NHCOCH_2NH_2$ | NT |
| 66 | $NHCOCH_2CH_2NH_2$ | NT |
| 67 | $NHCOCH(CH_3)NH_2$ | NT |
| 68 | $NHCOCH_2NHCH_3$ | NT |
| 69 | $NHCOCH_2CH_2NHCH_3$ | NT |
| 70 | $NHCOCH_2CH_2$-piperazinetBoc | NT |
| 71 | $NHCOCH_2CH_2NHCH_2CH_3$ | NT |
| 72 | $NHCOCH_2$-$N^t$BOC-Piperazine | NT |
| 73 | $NHCOCH_2$-piperazine-HCl | 61 |
| 74 | $NHCO(CH_2)_7NHCH_3$ | NT |
| 75 | $NHCOCH_2CO$-piperazine.HCl | 43 |
| 76 | $NHCOCH_2Cl$ | NT |
| 77 | $NHCOCH_2CH_2Cl$ | NT |
| 78 | $NHCOC_6H_4$—CH=CHCOOH | NT |
| 79 | NHCO(2,5-difluorophenyl)COOH | NT |
| 80 | $NHCOCH_2COOCH_3$ | NT |
| 81 | $NHCO(CH_2)_2COOCH_2CH_3$ | 59 |
| 82 | NHCOCOCOOH | NA |
| 83 | $NHCO(CH_2)_4COOCH_3$ | 64 |
| 84 | $NHCO(CH_2)_5COOCH_3$ | NT |
| 85 | $NHCO(CH_2)_6COOCH_3$ | 73 |
| 86 | $NHCO(p$-$C_6H_4CH$=$CHCOOCH_2CH_3)$ | NT |
| 87 | $NHCO(CH_2)_8COOCH_3$ | NT |
| 89 | NH(2-thiophenoyl) | 67 |
| 90 | NH(2-furoyl) | 55 |
| 91 | NH(m-chloromethylenebenzoyl) | 40 |
| 92 | NH(m-N,N-diethylmethylenebenzoyl) | 50 |
| 93 | NH(m-$NHCOCH_2Cl$-benzoyl) | 55 |

TABLE 1-continued

[Structure: isoindolin-1-one with NH and R substituent]

| Cmpd No. | R | % Inhibition (10 μM) |
|---|---|---|
| 94 | NH(m-NHCOCH$_2$N(CH$_2$CH$_3$)$_2$-benzoyl) | 45 |
| 95 | NH(m-NHCOCH$_2$N(CH$_3$)$_2$-benzoyl) | 50 |
| 96 | NH[m-CH2-(2-hydroxymethylenepyrrolidine)benzoyl] | 66 |
| 97 | NH[m-CH2-1,2,3,4-tetrahydroisoquinoline)-benzoyl] | 78 |
| 98 | NHCOCH2-isoindoline | 38 |
| 99 | NH(2-carboxybenzoyl) | 38 |
| 100 | NHCOCH$_2$CH(OTBDMS)CH$_2$COOH | NT |

Example 3

Effects of Substituted 2,3-dihydro-isoindol-1-ones on In Vivo Models of Reperfusion Injury In order to examine the efficacy of the compounds of the invention in ischemia-reperfusion conditions, the effect of selected compounds in a local model of reperfusion injury was examined. The ischemia-reperfusion conditions were induced by ligation and release of the superior mesenteric artery in a mouse model. The artery was occluded for 45 min, followed by reperfusion for 1 h. Following the end of the reperfusion, gut permeability was measured with the fluorescein isothiocyanate-conjugated dextran (FD4) method in everted gut sacks. See, e.g., Wang et al, J. Surg. Res. 79:39–46, 1998; Wattanasirichaigoon et al., Shock 12: 127–133, 1999; and Tamai et al., Alcohol Clin. Exp. Res. 24: 390–394, 2000. Ischemia-reperfusion increased the permeability of the gut from 9±2 to 245±46 ml/min/cm$^2$, indicating severe damage of the reperfused gut. Treatment with two compounds presented in Table 1 (above), where R$_1$ is H (compound 1) and NHCOCH$_2$-(S)-prolinol (compound 15) (20 mg/kg i.v., injected 10 min prior to the start of reperfusion), reduced the increase in the permeability of the gut to 82±9 and 54±11 mlmin/cm$^2$, respectively, indicating maintenance of gut function. The ischemia-reperfusion studies in the gut were associated with a <30% mortality, whereas >90% survival was noted in the animals treated with the compounds. These data indicate that the compounds of the invention have therapeutic effects in various systemic and local conditions of ischemia-reperfusion.

Example 4

Effects of Nucleoside Derivatives on In Vitro Inflammation Models:

The following example illustrates the ability of nucleoside derivatives to inhibit PARS activity. For example, when a nucleoside derivative is conjugated to a compound (such as a substituted isoindolinone derivative) that may have inherent anti-PARS activity, the conjugate may inhibit the enzyme more strongly that either of the parent moieties.

Derivatives with minor modifications to the ribose moiety (e.g., compounds 137–140 in Table 2) have only modest activity as does adenosine itself (compound G, Table 3). However, when coupled to cyclic moieties that have little or modest PARS inhibitory activity alone (e.g., the weaker of the isoindolinone derivatives shown in Table 1), the resultant compound frequently has unexpectedly good PARS inhibitory activity.

For example, conjugates of adenosine derivatives were investigated for PARS inhibition. Compounds 101–113 and 123–130 (Table 2) are far more potent than the adenosine derivatives 139 and 140 (Table 2) or isoindolinone compounds A and B (Table 3), from which compounds 101–113 and 123–130 are derived. It is apparent from compounds 101–130 that the nature of L, Z$_1$ and Z$_2$, influence the overall potency of the invention involving coupling of an inhibitor of PARS as group G to adenosine. Compounds 124 and 130 are the most potent derivatives of this series.

Compound 133 (Table 2) is more potent than both the adenosine derivative 139 (Table 2) and the biphenyl compounds F and E (Table 3) from which it was derived.

Compound 134 (Table 2) is more potent than both the adenosine derivative 139 (Table 2) and the known PARS inhibitor 3-aminobenzamide (E, table 3) from which it was formed.

Compounds 135 and 136 (Table 2) are more potent than either the adenosine derivative 139 (Table 2) or compound C (Table 3) from which they were formed.

Example 5

Effects of Nucleoside Derivatives on In Vivo Inflammation and Reperfusion Injury Models:

In order to examine the efficacy of the compounds of the invention in ischemia-reperfusion conditions, the effect of selected compounds in local models of reperfusion injury was examined.

Gut ischemia-reperfusion conditions were induced by ligation and release of the superior mesenteric artery in a mouse model. The artery was occluded for 45 min, followed by reperfusion for 1 h. Following the end of the reperfusion, gut permeability was measured with the FD4 method in everted gut sacks. Ischemia-reperfusion induced an approximately 25-fold increase in the permeability of the gut, indicating severe damage of the reperfused gut. Treatment with compounds 124 and 130, see Table 2 (below), (10 mg/kg i.v., injected 10 min prior to the start of reperfusion), markedly reduced the increase in the permeability of the gut to by 72 and 74%, respectively, indicating maintenance of the gut function. The ischemia-reperfusion studies in the gut were associated with a <30% mortality without treatment, whereas >80% survival was noted in the animals treated with the compounds. These data indicate that the compounds of the invention have therapeutic effects in various systemic and local conditions of ischemia-reperfusion.

In another set of experiments, the effect of compounds 124 and 130 in a rat model of middle cerebral artery occlusion/reperfusion were examined. Occlusion lasted for 2 hours, followed by reperfusion for 24 hours. Infarct size was quantified with tetrazolium staining and survival and neurological scores were monitored. The compounds were administered at 10 mg/kg i.v. 5 min before the start of reperfusion in one group, and continued at a rate of 10 mg/kg/h infusion during the reperfusion. Vehicle-treated animals (control) developed a >50% mortality over 24 hours, whereas <10% of the animals died in the drug treated groups. The compounds tested reduced the size of brain infarction by 64±2 and 57±3%, respectively. Vehicle treated animals that survived for 24 h developed severe neurological deficit (3–4 on a scale of 1–4), whereas in the animals treated with the compounds of the invention showed minor or no detectable deficit (0–1 on a scale of 1–4).

In another set of experiments, Male Wistar rats were anesthetized with thiopentone sodium (60 mg/kg, i.p.) and were subjected to myocardial infarction. The chest was opened at the fourth intercostal space and a 5.0 silk ligature was placed around the left anterior descending coronary artery for occlusion. Next, one hour of myocardial ischemia was performed, followed by 2 h reperfusion. Myocardial infarct size was quantified by tetrazolium staining. Treatment with compound 130, given at 20 mg/kg i.v. 10 min before the start of the reperfusion, reduced the infarct size by 35±7%, as measured at 2 hours of reperfusion.

Compounds 124 and 130 were also tested in a mouse model of local inflammation (colitis induced by oral exposure to dextran sulfate solution, DSS). The compounds were given as oral gavage at 10 mg/kg, twice a day. Vehicle-treated animals (control) developed significant mortality (>60% animals died over 3 weeks), whereas drug treated animals lived longer (<10% mortality at 3 weeks), and exhibited a lesser degree of intestinal inflammation, as evaluated by gross examination and histology (severity scores at least 50% reduced by both compounds). Compounds 124 and 130 also protected against endotoxin-induced lethality in a mouse model (an experimental model of systemic inflammation).

Taken together, the compounds tested exhibit significant protective effects in various models of local and systemic inflammation and reperfusion injury, and thus, are likely to exert beneficial effects in the human equivalent of these diseases.

TABLE 2

| Cmpd. # | Compound Structure | Inhibition at 100 μM | Inhibition at 10 μM |
|---|---|---|---|
| 101 | TFA salt (isoindolinone-NH-CO-CH2-CO-NH-CH2-ribose-adenine) | 100 | 64 |
| 102 | isoindolinone-NHCO(CH2)2CONH-CH2-ribose-adenine | 100 | 100 |
| 103 | isoindolinone-NHCO(CH2)3CONH-CH2-ribose-adenine | 99 | 88 |

TABLE 2-continued
| Cmpd. # | Compound Structure | Inhibition at 100 µM | Inhibition at 10 µM |
|---|---|---|---|
| 104 | 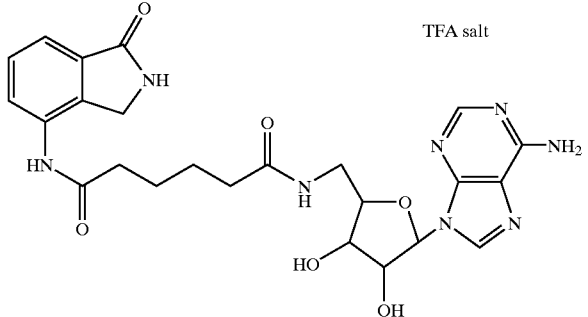 TFA salt | 100 | 67 |
| 105 | 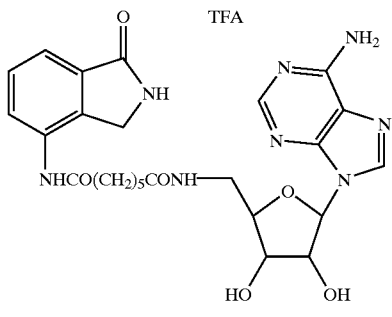 TFA | 100 | 66 |
| 106 | 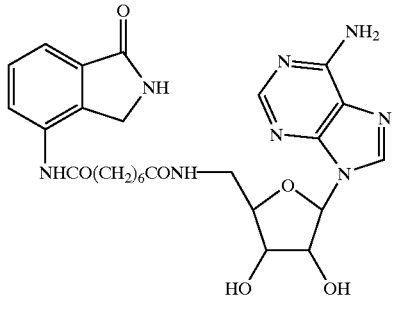 | 100 | 98 |
| 107 | 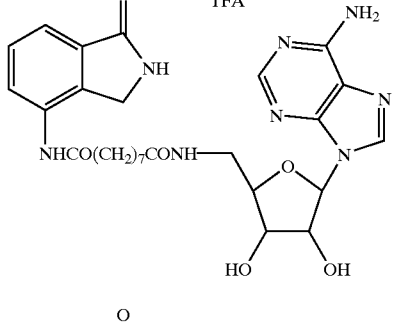 TFA | 100 | 62 |
| 108 | 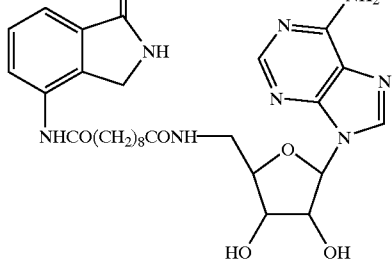 | 74 | 34 |

TABLE 2-continued

| Cmpd. # | Compound Structure | Inhibition at 100 μM | Inhibition at 10 μM |
|---|---|---|---|
| 109 | 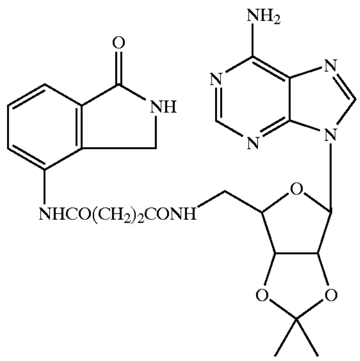 | 60 | 29 |
| 110 | 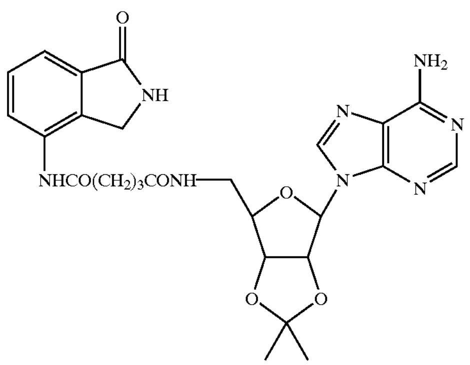 | 64 | 29 |
| 111 | 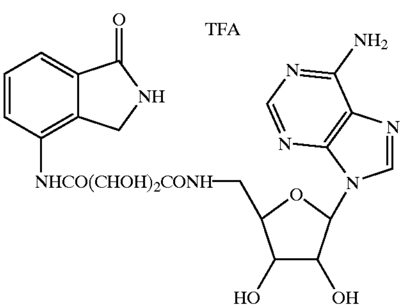 | 100 | 75 |
| 112 | 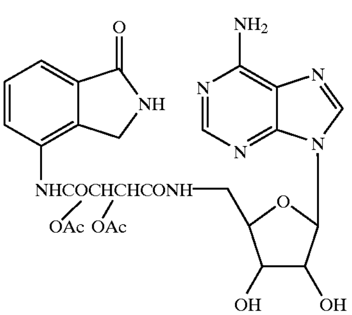 | 100 | 73 |

TABLE 2-continued
| Cmpd. # | Compound Structure | Inhibition at 100 μM | Inhibition at 10 μM |
|---|---|---|---|
| 113 | 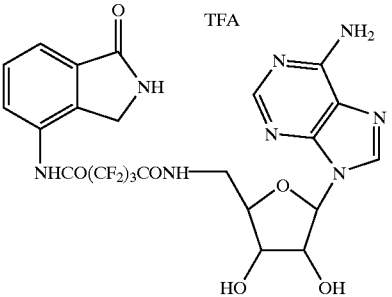 | 85 | 55 |
| 114 | 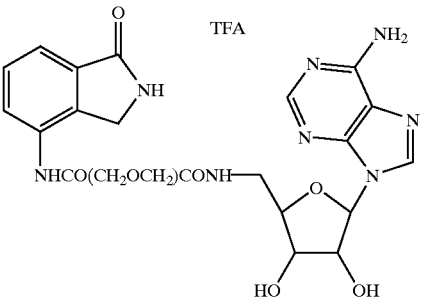 | 100 | 56 |
| 115 | 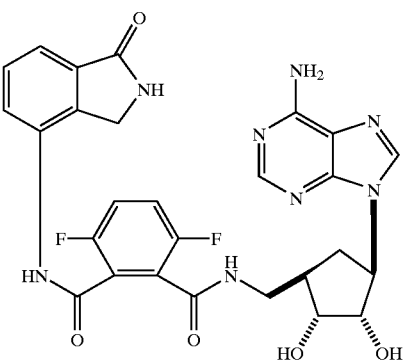 | 34 | 0 |
| 116 | 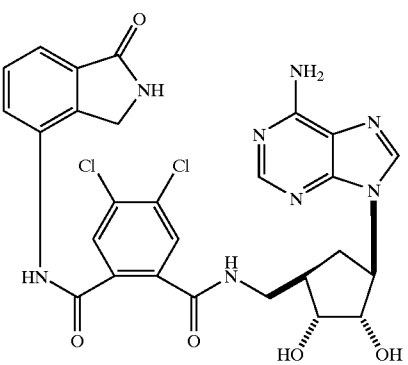 | 55 | 0 |

TABLE 2-continued

| Cmpd. # | Compound Structure | Inhibition at 100 μM | Inhibition at 10 μM |
|---|---|---|---|
| 117 | 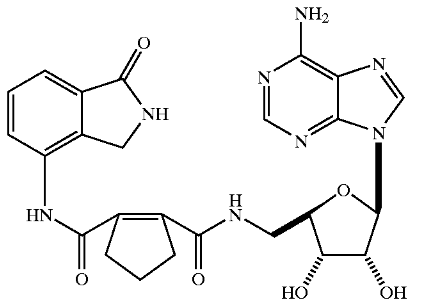 | NT | NT |
| 118 | 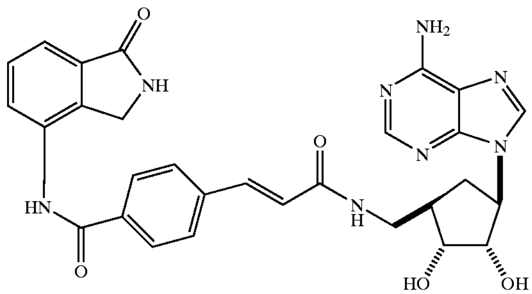 | 51.4 | 31.3 |
| 119 | 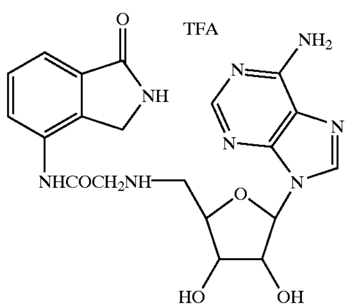 | 58 | 25 |
| 120 | 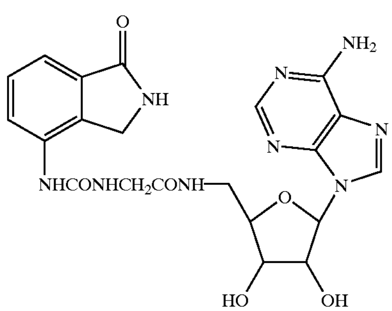 | 100 | 62 |
| 121 | 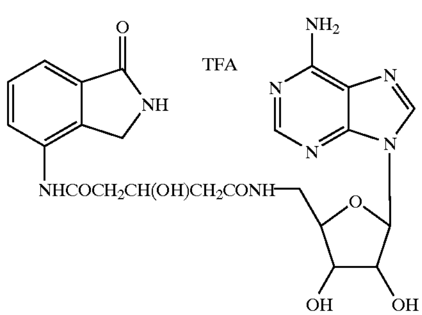 | 81 | 13.3* |

TABLE 2-continued

| Cmpd. # | Compound Structure | Inhibition at 100 μM | Inhibition at 10 μM |
|---|---|---|---|
| 122 | 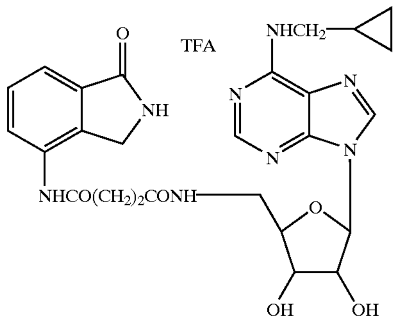 | NT | 25* |
| 123 | 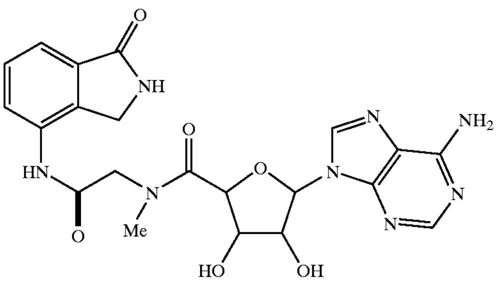 | NT | 74* |
| 124 | 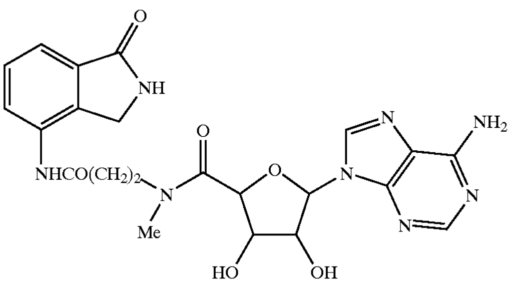 | 100 at 200 nm | 87.1* |
| 125 | 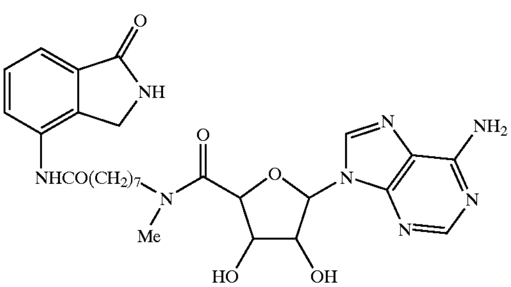 | NT | 70* |
| 126 | 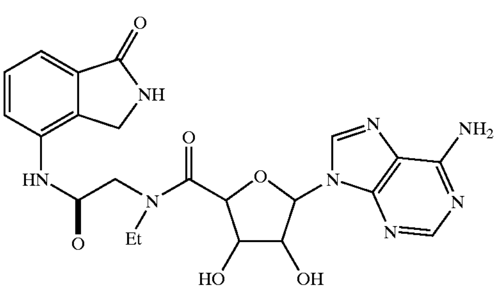 | NT | 67.1* |

TABLE 2-continued

| Cmpd. # | Compound Structure | Inhibition at 100 μM | Inhibition at 10 μM |
|---|---|---|---|
| 127 | 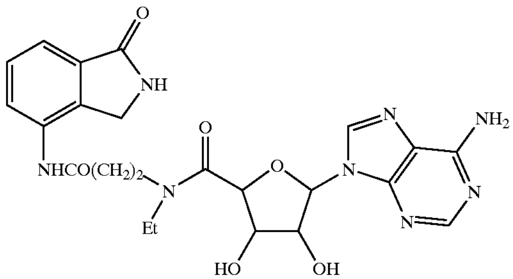 | NT | 89* |
| 128 | 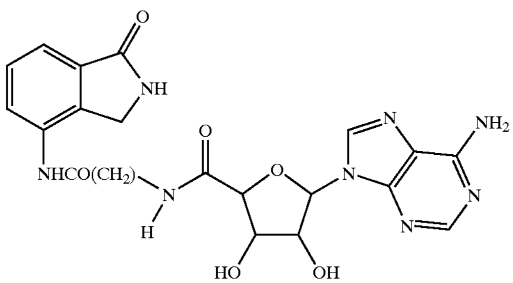 | NT | 83.2* |
| 129 | 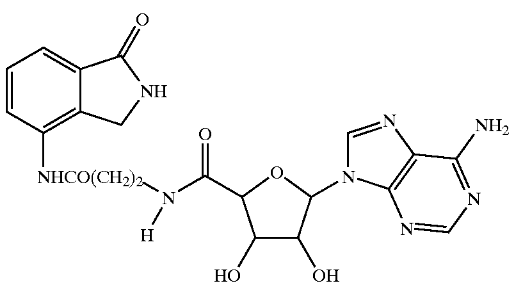 | NT | 77.4* |
| 130 | 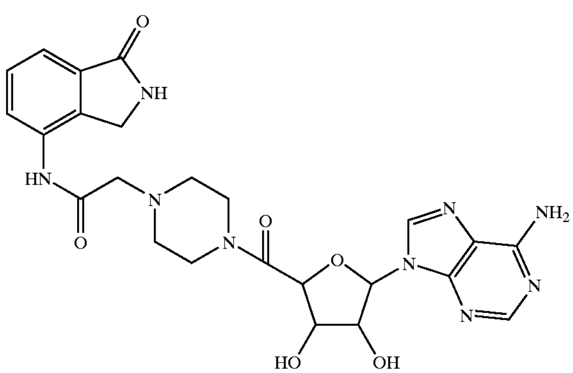 | 100 at 200 nm | 97* |
| 131 | 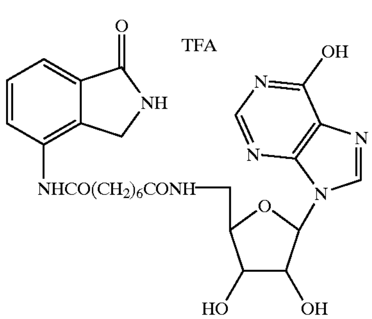 | 68 | 36 |

TABLE 2-continued

| Cmpd. # | Compound Structure | Inhibition at 100 μM | Inhibition at 10 μM |
|---|---|---|---|
| 132 | (isoindolin-1-one-4-yl)-NHCO(CH$_2$)$_2$CONH-CH$_2$-(ribose)-cytosine | 83 | 61 |
| 133 | 2'-carbamoyl-biphenyl-3-yl-NHCO(CH$_2$)$_2$CONH-CH$_2$-(ribose)-adenine | 69 | 5 |
| 134 | 3-carbamoylphenyl-NHCO(CH$_2$)$_2$CONH-CH$_2$-(ribose)-adenine | 73 | 52 |
| 135 | (4-oxo-4,5,6,7-tetrahydroindol-1-yl)-CH$_2$CH$_2$CONH-CH$_2$-(2',3'-isopropylidene-ribose)-adenine | 25 | 15 |

TABLE 2-continued

| Cmpd. # | Compound Structure | Inhibition at 100 μM | Inhibition at 10 μM |
|---|---|---|---|
| 136 | (structure) | 42 | 32 |
| 137 | (structure) | 40 | 21 |
| 138 | (structure) | 11.5 | 0 |
| 139 | (structure) | 27 | NT |
| 140 | (structure) | NT | 14.2 |

TABLE 3

| COMPOUND | STRUCTURE | INHIBITION at 10 μM |
|---|---|---|
| A (1) | isoindolin-1-one | 33 |
| B (4) | 4-amino-isoindolin-1-one | 27 |
| C | 1-(2-carboxyethyl)-4-oxo-4,5,6,7-tetrahydroindole | 4 |
| D | 3-aminobenzamide | 28 |
| E | 2'-nitro-[1,1'-biphenyl]-2-carboxamide | 35 |
| F | 3'-amino-[1,1'-biphenyl]-2-carboxamide | 37 |
| G | adenosine | 40 |

OTHER EMBODIMENTS

From the above description, one skilled in the art can easily ascertain the essential characteristics of the present invention. Without departing from the spirit and scope thereof, one of ordinary skill in the art can make various changes and modifications of the invention to adapt it to various uses and conditions. Other embodiments are also within the claims.

What is claimed is:

1. A compound having the formula:

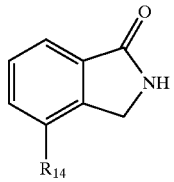

or a pharmaceutically acceptable base or acid addition salt, hydrate, stereoisomer, or mixture thereof, wherein:

$R_{14}$ is hydroxy, —OCH$_3$, —CH$_2$NH$_2$ or —Q—B—D;

Q is NHCO, NHCONH, O, OCO, NH, CH$_2$NH or NHCO—C$_1$-C$_8$ straight or branched chain alkylene;

B is C$_1$-C$_8$ straight or branched chain alkylene, CH=CH, cyclohexyl, phenyl, C$_1$-C$_2$ straight or branched chain alkyl-NH, NH, phenylene, phenyl-CH$_2$, phenyl-NHCO, O—CH$_2$, —CO—, —CO$_2$—, —CONH—, —C(O)—C(O)—, —CONHCH$_2$—, —NHCO— or —(CF$_2$)$_3$—;

D is hydrogen, halogen, hydroxy, cyclohexyl, C$_1$-C$_{10}$ straight or branched chain alkyl, —C$_1$-C$_4$ straight or branched chain alkyl-N(R$^{18}$)$_2$, —N(R$^{18}$)$_2$, —CH=CHCOOR$^{19}$, —NHC(=NH)NH$_2$, —NHC(=NH)N—COO-t-butyl, —COOR$^{19}$, —NHCOR$^{19}$, —CONHR$^{18}$, phenyl, piperidinyl, anilinyl, piperazinyl, pyrolyl, imidazolyl, benzimidazolyl, tetrazolyl, indolyl, isoquinolinyl, quinolinyl, pyrrolidinyl, purinyl, pyrimidinyl, morpholinyl, thiophenyl, furanyl, isoindolinyl, pyridinyl, prolinyl or nipecotyl;

R$^{18}$ is hydrogen, methyl, ethyl, benzyl, cyclohexyl, —COO-t-butyl, C$_1$-C$_2$ alkylene-piperidinyl, C$_1$-C$_2$ alkylene-pyridinyl or C$_1$-C$_2$ alkylene-benzimidazolyl; and R$^{19}$ is hydrogen, methyl, ethyl or —CH(NH-cyclohexyl)$_2$;

wherein each alkyl, alkylene, phenyl, phenylene, piperidinyl, purinyl, isoquinolinyl, indolyl or imidazolyl group is independently unsubstituted or substituted with one or more of the following groups: -halogen, methyl, ethyl, —OCH$_3$, —COOH, —COOCH$_3$, nitro, —N(CH$_3$)$_2$, —CH$_2$-halo, —NHCOCH$_2$-halo, NHCOCH$_2$—N(CH$_3$)$_2$, —O—Si(CH$_3$)$_2$(t-butyl), —O—CH$_3$, —OC(O)CH$_3$, —COO-t-butyl or —CH$_2$—NH—COO-t-butyl.

2. The compound of claim 1 wherein R$^{14}$ is selected from the group consisting of NHCOCH$_2$Cl, NHCOCH$_2$N(CH$_3$)$_2$, NHCOCH$_2$N(CH$_2$CH$_3$)$_2$, NHCOCH$_2$N(CH$_3$)-piperazine, NHCOCH$_2$CH$_2$CH$_2$N(CH$_3$)-piperazine, NHCOCH$_2$NH(CH$_2$CH$_3$), NHCOCH$_2$-piperidine, NHCOCH$_2$-1,2,3,4-tetrahydroisoquinoline, NHCOCH$_2$N(CH$_3$)CH$_2$Ph, NHCOCH$_2$(S)-prolinol, NHCOCH$_2$-9-adenine, NHCOCH$_2$-9-(6-chloropurine), NHCOCH$_2$-9-(6-N,N-dimethylpurine), NHCOCH$_2$-benzimidazole, NHCOCH$_2$-ethylnipecotate, NHCOCH$_2$-morpholine, NHCOCH$_2$-pyrrolidine, NHCOCH$_2$-1,2,3,4-tetrahydro-6,7-dimethoxyisoquinoline, NHCOCH$_2$-4-indolemethylester, NHCO-m-NO$_2$-benzoyl, NHCOCH$_2$CH$_2$COOC(NH-cyclohexyl)$_2$, OH, OCH$_3$, OCH$_2$COOCH$_3$, OCH$_2$COOH, OCH$_2$CO-1,2,3,4-tetrahydroisoquinoline, OCO-m-NO$_2$- benzoyl, $CH_2NH_2$, $CH_2NHCO$-m-$NO_2$-benzoyl, $NHCOCH_2CH_2CH_2COOH$, $NHCOCH=CHCOOH$, $NHCOCH_2CH_2CO$-1,2,3,4-tetrahydroisoquinoline, $NHCOCH_2CH_2CH_2CO$-1,2,3,4-tetrahydroisoquinoline, $NHCOCH_2CH_2OH$, $NHCOCH_2CH_2CH_2OH$, NHCONH-cyclohexyl, $NHCO(CH_2)_4NHtBOC$, $NHCOCH_2CH_2CH_2CH_2NH_2$, $NHCOCHNHtBoc(CH_2)_3$—NH—C=NHN'Boc), $NHCOCHNH_2(CH_2)_3$-guanidine, NHCOCHNH'Boc(5-$CH_2$—N-tBoc-imidazole), NHCOCHNH'Boc(3-$CH_2$-indole), NH-prolinyl, NH-nipecotyl, NH-3,4,5-trimethoxybenzoyl, $NHCOCH_2CH_2CONH$(2-$CH_2$-benzimidazole), $NHCO(CH_2)_2CONH(CH_2)_2$-piperidine, $NHCO(CH_2)_2CONH(CH_2)_2$-piperidine, $NHCO(CH_2)_2CONH(CH_2)_2$-2-pyridine, $NHCOCH(NHCOOC_7H_7)(CH_2)_4NHtBOc$, $NHCOCH(NHCOOC_7H_7)(CH_2)_4NH_2$, $NHCOCH_2COOH$, $NHCO(CH_2)_2COOH$, $NHCO(CH_2)_3COOH$, $NHCO(CH_2)_3COOH$, $NHCO(CH_2)_4COOH$, $NHCO(CH_2)_5COOH$, $NHCO(CH_2)_6COOH$, $NHCO(CH_2)_7COOH$, $NHCO(CH_2)_8COOH$, $NHCO(CHOAc)_2COOH$, $NHCO(CF_2)_3COOH$, $NHCONHCH_2COOH$, $NHCOCH_2OCH_2COOH$, $NHCOCH_2NH_2$, $NHCOCH_2CH_2NH_2$, $NHCOCH(CH_3)NH_2$, $NHCOCH_2NHCH_3$, $NHCOCH_2CH_2NHCH_3$, $NHCOCH_2$tBOC-piperazine, $NHCOCH_2$-piperazine-HCl, $NHCO(CH_2)_7NHCH_3$, $NHCOCH_2CO$-piperazine-HCl, $NHCOCH_2CH_2Cl$, $NHCOCH_2CH_2CH_2Cl$, $NHCOC_6H_4COCH=CHCOOH$, NHCO(2,5-difluorophenyl)COOH, $NHCOCH_2COOCH_3$, $NHCO(CH_2)_2COOCH_2CH_3$, $NHCOCOCOOCH_3$, $NHCO(CH_2)_4COOCH_3$, $NHCO(CH_2)CH_3$, $NHCO(CH_2)_6COOCH_3$, NHCO(p-$C_6H_4$—CH=CHCOOCH$_2$CH$_3$), $NHCO(CH_2)_8COOCH_3$, NH(2-thiophenoyl), NH(2-furoyl), NH(m-chloromethylenebenzoyl), NH(m-N,N-diethylmethylenebenzoyl), NH(m-$NHCOCH_2$Cl-benzoyl), NH(m-$NHCOCH_2N(CH_2CH_3)_2$-benzoyl), NH(m-$NHCOCH_2N(CH_3)_2$-benzoyl), NH-[m-$CH_2$-(2-hydroxymethylenepyrrolidine)-benzoyl], NH-[m-$CH_2$-(1,2,3,4-tetrahydroisoquinoline)-benzoyl]$NHCOCH_2$-isoindoline, NH-2-carboxybenzoyl, and $NHCOCH_2CH$(OTBDMS)-$CH_2COOH$.

3. A method of treating an inflammatory disease in a subject, the method comprising administering to a subject in need of inflammatory-disease treatment, a compound in an amount sufficient to treat the inflammatory disease, the compound having the formula:

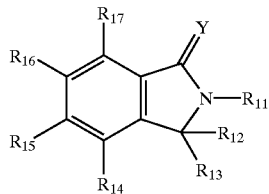

or a pharmaceutically acceptable base or acid addition salt, hydrate, stereoisomer, or mixture thereof, wherein:

Y is O, S, Se, NH, —$C_1$–$C_{10}$ straight or branched chain alkyl or N-aryl;

$R_{11}$ is hydrogen, —OH, —$C_1$–$C_{10}$ straight or branched chain alkyl or the side chain of a naturally occurring amino acid;

$R_{12}$ and $R_{13}$ are, independently, hydrogen, —$C_1$–$C_{10}$ straight or branched chain alkyl, aryl, —OH, —O—$C_1$–$C_{10}$ straight or branched chain alkyl, —O-aryl, , —N-aryl, piperidinyl, anilinyl, piperazinyl, pyrolyl, imidazolyl, benzimidazolyl, tetrazolyl, indolyl, isoquinolinyl, quinolinyl, pyrrolidinyl, purinyl, pyrimidinyl, morpholinyl, thiophenyl, furanyl, isoindolinyl, pyridinyl, prolinyl, nipecotyl, or taken together, form =O, =NH or =S;

$R_{14}$, $R_{15}$, $R_{16}$, and $R_{17}$ are, independently, hydrogen, halogen, —$C_1$–$C_{10}$ straight or branched chain alkyl, —$C_1$–$C_{10}$ straight or branched chain alkylhalo, -hydroxy, —O—$C_1$–$C_{10}$ straight or branched chain alkyl, —$C_2$–$C_{10}$ straight or branched chain alkenyl group, —$C_3$–$C_8$ carbocycle, aryl, —$C_1$–$C_{10}$ straight or branched chain alkylamino, amino, carboxy, ester, —$C_1$–$C_{10}$ straight or branched chain alkyl-$NH_2$-aryl-$C_1$–$C_{10}$ straight or branched chain alkyl, nitro, or —Q—B—D;

wherein Q is NHCO, NHCONH, O, CO, $OCO_2$, OCO, OCONH, NH, $CH_2$, $C_1$–$C_{10}$ straight or branched chain alkylene, $NHCO_2$, S, $SO_2$, CS or SO;

B is $C_1$–$C_{10}$ straight or branched chain alkylene, $C_2$–$C_{10}$ straight or branched chain alkenylene, $C_3$–$C_8$ carbocyclo, arylene, NH, $C_1$–$C_{10}$ straight or branched chain alkylamido, arylamido, or aryl-$C_1$–$C_{10}$ straight or branched chain alkylene, $C_1$–$C_{10}$ straight or branched chain alkylene-NH, $C_1$–$C_{10}$ straight or branched chain alkylene-NHCO, arylene-NHCO, —O—$C_1$–$C_{10}$ straight or branched chain alkylene, —CO—, —$CO_2$—, —CONH—, —NHC(O)—C(O)—, —CONH—$C_1$–$C_{10}$ straight or branched chain alkylene-, —NHCO—, or —$(CF_2)_3$—, which may be optionally substituted with with one or more substituents chosen from the following groups: hydrogen, halogen, $C_1$–$C_{10}$ straight or branched chain alkylhalo, hydroxy, nitro, amino or amido;

D is hydrogen, halogen, —$COOR^{18}$ or hydroxy, or a substituted amido, $C_3$–$C_8$ carbocycle, $C_1$–$C_{10}$ straight or branched chain alkylamine, amine or, wherein said substitutions are selected from the group consisting of hydrogen, $C_1$–$C_{10}$ straight or branched chain alkylhalo, $C_1$–$C_{10}$ straight or branched chain alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, $C_3$–$C_8$ carbocyclic, aryl, benzyl, $C_1$–$C_{10}$ straight or branched chain alkylamino, $C_1$–$C_{10}$ straight or branched chain alkylamido, aryl-$C_1$–$C_{10}$ straight or branched chain alkyl, piperidinyl, piperazinyl, pyrolyl, imidazolyl, benzimidazolyl, tetrazolyl, indolyl, isoquinolinyl, quinolinyl, pyrrolidinyl, purinyl, pyrimidinyl, morpholinyl, thiophenyl, furanyl, isoindolinyl, pyridinyl, prolinyl or nipecotyl;

$R^{18}$ is hydrogen, $C_1$–$C_{10}$ straight or branched chain alkylhalo, $C_1$–$C_{10}$ straight or branched chain alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, $C_3$–$C_8$ carbocyclic, aryl, benzyl, $C_1$–$C_{10}$ straight or branched chain alkylamino, $C_1$–$C_{10}$ straight or branched chain alkylamido, aryl-$C_1$–$C_{10}$ straight or branched chain alkyl, piperidinyl, piperazinyl, pyrolyl, imidazolyl, benzimidazolyl, tetrazolyl, indolyl, isoquinolinyl, quinolinyl, pyrrolidinyl, purinyl, pyrimidinyl, morpholinyl, thiophenyl, furanyl, isoindolinyl, pyridinyl, prolinyl or nipecotyl;

wherein said inflammatory disease is rheumatoid arthritis, osteoarthritis, a bone disease associated with increased bone resorption, ileitis, ulcerative colitis, Barrett's syndrome, Crohn's disease, asthma, adult respiratory stress syndrome, chronic obstructive airway disease, multiple sclerosis, AIDS-related neurodegeneration, Alzheimer's disease, gingivitis, periodontitis, infectious meningitis, encephalomyelitis, Parkinson's disease, Huntington's disease, amylotrophic lateral sclerosis, viral encephalitis, autoimmune encephalitis, diabetes mellitus, corneal dystrophy, trachoma, onchocerciasis, uveitis, sympathetic ophthalmitis or endophthalmitis.

4. The method of claim 3, wherein said subject is a human subject.

5. The method of claim 3, wherein said compound is administered systemically.

6. The method of claim 3, wherein said compound is administered topically.

7. The method of claim 3, where said inflammatory disease is caused by a condition selected from the group consisting of gram-positive shock, gram-negative shock, hemorrhagic shock, anaphlactic shock, traumatic shock and chemotherapeutic shock.

8. A method of treating or preventing reperfusion injury in a subject, the method comprising administering a compound in an amount sufficient to inhibit reperfusion injury in said subject, the compound having the formula:

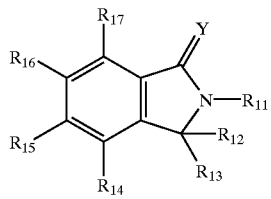

or a pharmaceutically acceptable base or acid addition salt, hydrate, stereoisomer, or mixture thereof, wherein:

Y is O, S, Se, NH, —$C_1$–$C_{10}$ straight or branched chain alkyl or N-aryl;

$R_{11}$ is hydrogen, —OH, —$C_1$–$C_{10}$ straight or branched chain alkyl or the side chain of a naturally occurring amino acid;

$R_{12}$ and $R_{13}$ are, independently, hydrogen, —$C_1$–$C_{10}$ straight or branched chain alkyl, aryl, —OH, —O—$C_1$–$C_{10}$ straight or branched chain alkyl, —O-aryl, , —N-aryl, piperidinyl, anilinyl, piperazinyl, pyrolyl, imidazolyl, benzimidazolyl, tetrazolyl, indolyl, isoquinolinyl, quinolinyl, pyrrolidinyl, purinyl, pyrimidinyl, morpholinyl, thiophenyl, furanyl, isoindolinyl, pyridinyl, prolinyl, nipecotyl, or taken together, form =O, =NH or =S;

$R_{14}$, $R_{15}$, $R_{16}$, and $R_{17}$ are, independently, hydrogen, halogen, —$C_1$–$C_{10}$ straight or branched chain alkyl, —$C_1$–$C_{10}$ straight or branched chain alkylhalo, -hydroxy, —O—$C_1$–$C_{10}$ straight or branched chain alkyl, —$C_2$–$C_{10}$ straight or branched chain alkenyl group, —$C_3$–$C_8$ carbocycle, aryl, —$C_1$–$C_{10}$ straight or branched chain alkylamino, amino, carboxy, ester, —$C_1$–$C_{10}$ straight or branched chain alkyl-$NH_2$, -aryl-$C_1$–$C_{10}$ straight or branched chain alkyl, nitro, or —Q—B—D;

wherein Q is NHCO, NHCONH, O, CO, $OCO_2$, OCO, OCONH, NH, $CH_2$, $C_1$–$C_{10}$ straight or branched chain alkyene, $NHCO_2$, S, $SO_2$, CS or SO;

B is $C_1$–$C_{10}$ straight or branched chain alkylene, $C_2$–$C_{10}$ straight or branched chain alkenylene, $C_3$–$C_8$ carbocyclo, arylene, NH, $C_1$–$C_{10}$ straight or branched chain alkylamido, arylamido, or aryl-$C_1$–$C_{10}$ straight or branched chain alkylene, $C_1$–$C_{10}$ straight or branched chain alkylene-NH, $C_1$–$C_{10}$ straight or branched chain alkylene-NHCO, arylene-NHCO, —O—$C_1$–$C_{10}$ straight or branched chain alkylene, —CO—, —$CO_2$—, —CONH—, —NHC(O)—C(O)—, —CONH—$C_1$–$C_{10}$ straight or branched chain alkylene-, —NHCO—, or —$(CF_2)_3$—, which may be optionally substituted with with one or more substituents chosen from the following groups: hydrogen, halogen, $C_1$–$C_{10}$ straight or branched chain alkylhalo, hydroxy, nitro, amino or amido;

D is hydrogen, halogen, —$COOR^{18}$ or hydroxy, or a substituted amido, $C_3$–$C_8$ carbocycle, $C_1$–$C_{10}$ straight or branched chain alkylamine, amine or, wherein said substitutions are selected from the group consisting of hydrogen, $C_1$–$C_{10}$ straight or branched chain alkylhalo, $C_1$–$C_{10}$ straight or branched chain alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, $C_3$–$C_8$ carbocyclic, aryl, benzyl, $C_1$–$C_{10}$ straight or branched chain alkylamino, $C_1$–$C_{10}$ straight or branched chain alkylamido, aryl-$C_1$–$C_{10}$ straight or branched chain alkyl, piperidinyl, piperazinyl, pyrolyl, imidazolyl, benzimidazolyl, tetrazolyl, indolyl, isoquinolinyl, quinolinyl, pyrrolidinyl, purinyl, pyrimidinyl, morpholinyl, thiophenyl, furanyl, isoindolinyl, pyridinyl, prolinyl or nipecotyl;

$R^{18}$ is hydrogen, $C_1$–$C_{10}$ straight or branched chain alkylhalo, $C_1$–$C_{10}$ straight or branched chain alkylhydroxy, $C_1$–$C_{10}$ straight or branched chain alkyl, $C_2$–$C_{10}$ straight or branched chain alkenyl group, $C_2$–$C_{10}$ straight or branched chain alkynyl group, $C_3$–$C_8$ carbocyclic, aryl, benzyl, $C_1$–$C_{10}$ straight or branched chain alkylamino, $C_1$–$C_{10}$ straight or branched chain alkylamido, aryl-$C_1$–$C_{10}$ straight or branched chain alkyl, piperidinyl, piperazinyl, pyrolyl, imidazolyl, benzimidazolyl, tetrazolyl, indolyl, isoquinolinyl, quinolinyl, pyrrolidinyl, purinyl, pyrimidinyl, morpholinyl, thiophenyl, furanyl, isoindolinyl, pyridinyl, prolinyl or nipecotyl.

9. The method of claim 8, wherein said compound is administered therapeutically.

10. The method of claim 8, wherein said reperfusion injury is myocardial infarction.

11. The method of claim 8, wherein said reperfusion injury is cardiopulmonary bypass.

12. The method of claim 8, wherein said reperfusion injury is stroke.

13. The method of claim 8, wherein said subject is a human subject.

14. The method of claim 8, wherein said administering is topical.

15. The method of claim 3, wherein the compound has the formula:

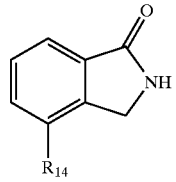

or a pharmaceutically acceptable base or acid addition salt, hydrate, stereoisomer, or mixture thereof, wherein:

$R_{14}$ is hydrogen, halogen, nitro, $NH_2$, hydroxy, —$OCH_3$, —$CH_2NH_2$ or —Q—B—D;

Q is NHCO, NHCONH, O, OCO, NH, $CH_2$ or NHCO—$C_1$–$C_8$ straight or branched chain alkylene;

B is $C_1$–$C_8$ straight or branched chain alkylene, CH=CH, cyclohexyl, phenyl, $C_1$–$C_2$ straight or branched chain alkyl-NH, NH, phenylene, phenyl-$CH_2$, phenyl-NHCO, O—$CH_2$, —CO—, —$CO_2$—, —CONH—, —C(O)—C(O)—, —CONH$CH_2$—, —NHCO— or —$(CF_2)_3$—;

D is hydrogen, halogen, hydroxy, cyclohexyl, $C_1$–$C_{10}$ straight or branched chain alkyl, —$C_1$–$C_4$ straight or branched chain alkyl-$N(R^{18})_2$, —$N(R^{18})_2$, —CH=CHCOO$R^{19}$, —NHC(=NH)$NH_2$, —NHC(=NH)N—COO-t-butyl, —COO$R^{19}$, —NHCO$R^{19}$, —CONH$R^{18}$, phenyl, piperidinyl, anilinyl, piperazinyl, pyrolyl, imidazolyl, benzimidazolyl, tetrazolyl, indolyl, isoquinolinyl, quinolinyl, pyrrolidinyl, purinyl, pyrimidinyl, morpholinyl, thiophenyl, furanyl, isoindolinyl, pyridinyl, prolinyl or nipecotyl, with the proviso that when Q is $CH_2$ and B is a bond or $C_1$–$C_8$ straight or branched chain alkylene, D is not hydrogen or $C_1$–$C_{10}$ straight or branched chain alkyl;

$R^{18}$ is —H, methyl, ethyl, benzyl, cyclohexyl, —COO-t-butyl, $C_1$–$C_2$ alkylene-piperidinyl, $C_1$–$C_2$ alkylene-pyridinyl or $C_1$–$C_2$ alkylene-benzimidazolyl; and $R^{19}$ is hydrogen, methyl, ethyl or —CH(NH-cyclohexyl)$_2$;

wherein each alkyl, alkylene, phenyl, phenylene, piperidinyl, purinyl, isoquinolinyl, indolyl or imidazolyl group is independently unsubstituted or substituted with one or more of the following groups: -halogen, methyl, ethyl, —$OCH_3$—COOH, —$COOCH_3$, nitro, —$N(CH_3)_2$, —$CH_2$-halo, —NHCO$CH_2$-halo, NHCO$CH_2$—$N(CH_3)_2$, —O—Si$(CH_3)_2$(t-butyl), —O—$CH_3$, —OC(O)$CH_3$, —COO-t-butyl or —$CH_2$—NH—COO-t-butyl.

16. The method of claim 15, wherein $R^{14}$ is selected from the group consisting of H, F, $NH_2$, $NO_2$, NHCO$CH_2$Cl, NHCO$CH_2$N$(CH_3)_2$, NHCO$CH_2$N$(CH_2CH_3)_2$, NHCO$CH_2$N($CH_3$)-piperazine, NHCO$CH_2CH_2CH_2$N($CH_3$)-piperazine, NHCO$CH_2$NH($CH_2CH_3$), NHCO$CH_2$-piperidine, NHCO$CH_2$-1,2,3,4-tetrahydroisoquinoline, NHCO$CH_2$N($CH_3$)$CH_2$Ph, NHCO$CH_2$(S)-prolinol, NHCO$CH_2$-9-adenine, NHCO$CH_2$-9-(6-chloropurine), NHCO$CH_2$-9-(6-N,N-dimethylpurine), NHCO$CH_2$-benzimidazole, NHCO$CH_2$-ethylnipecotate, NHCO$CH_2$-morpholine, NHCO$CH_2$-pyrrolidine, NHCO$CH_2$-1,2,3,4-tetrahydro-6,7-dimethoxyisoquinoline, NHCO$CH_2$-4-indolemethylester, NHCO-m-$NO_2$-benzoyl, NHCO$CH_2CH_2$COOC(NH-cyclohexyl)$_2$, OH, $OCH_3$, O$CH_2$COO$CH_3$, O$CH_2$COOH, O$CH_2$CO-1,2,3,4-tetrahydroisoquinoline, OCO-m-$NO_2$-benzoyl, $CH_2NH_2$, $CH_2$NHCO-m-$NO_2$-benzoyl, NHCO$CH_2CH_2CH_2$COOH, NHCOCH=CHCOOH, NHCO$CH_2CH_2$CO-1,2,3,4-tetrahydroisoquinoline, NHCO$CH_2CH_2CH_2$CO-1,2,3,4-tetrahydroisoquinoline, NHCO$CH_2CH_2$OH, NHCO$CH_2CH_2$OH, NHCONH-cyclohexyl, NHCO$(CH_2)_4$NHtBOC, NHCO$CH_2CH_2CH_2CH_2NH_2$, NHCOCHNHtBoc$(CH_2)_3$—NH—C=NHN′Boc), NHCOCHN$H_2(CH_2)_3$-guanidine, NHCOCHNH′Boc(5-$CH_2$—N-tBoc-imidazole), NHCOCHNH′Boc(3-$CH_2$-indole), NH-prolinyl, NH-nipecotyl, NH-3,4,5-trimethoxybenzoyl, NHCO$CH_2CH_2$CONH(2-$CH_2$-benzimidazole), NHCO$(CH_2)_2$CONH$(CH_2)_2$-piperidine, NHCO$(CH_2)_2$CONH$(CH_2)_2$-piperidine, NHCO$(CH_2)_2$CONH$(CH_2)_2$-2-pyridine, NHCOCH(NHCOO$C_7H_7$)$(CH_2)_4$NHtBOc, NHCOCH(NHCOO$C_7H_7$)$(CH_2)_4NH_2$, NHCO$CH_2$COOH, NHCO$(CH_2)_2$COOH, NHCO$(CH_2)_3$COOH, NHCO$(CH_2)_3$COOH, NHCO$(CH_2)_4$COOH, NHCO$(CH_2)_5$COOH, NHCO$(CH_2)_6$COOH, NHCO$(CH_2)_7$COOH, NHCO$(CH_2)_8$COOH, NHCO(CHOAc)$_2$COOH, NHCO$(CF_2)_3$COOH, NHCONH$CH_2$COOH, NHCO$CH_2$O$CH_2$COOH, NHCO$CH_2NH_2$, NHCO$CH_2CH_2NH_2$, NHCOCH($CH_3$)$NH_2$, NHCO$CH_2$NH$CH_3$, NHCO$CH_2CH_2$NH$CH_3$, NHCO$CH_2$tBOC-piperazine, NHCO$CH_2$-piperazine-HCl, NHCO$(CH_2)_7$NH$CH_3$, NHCO$CH_2$CO-piperazine-HCl, NHCO$CH_2CH_2$Cl, NHCO$CH_2CH_2CH_2$Cl, NHCO$C_6H_4$COCH=CHCOOH, NHCO(2,5-difluorophenyl)COOH, NHCO$CH_2$COO$CH_3$, NHCO$(CH_2)_2$ COO$CH_2CH_3$, NHCOCOCOO$CH_3$, NHCO$(CH_2)_4$COO$CH_3$, NHCO$(CH_2)CH_3$, NHCO$(CH_2)_6$COO$CH_3$, NHCO(p-$C_6H_4$—CH=CHCOO$CH_2CH_3$), NHCO$(CH_2)_8$COO$CH_3$, NH(2-thiophenoyl), NH(2-furoyl), NH(m-chloromethylenebenzoyl), NH(m-N,N-diethylmethylenebenzoyl), NH(m-NHCO$CH_2$Cl-benzoyl), NH(m-NHCO$CH_2$N$(CH_2CH_3)_2$-benzoyl), NH(m-NHCO$CH_2$N$(CH_3)_2$-benzoyl), NH-[m-$CH_2$-(2-hydroxymethylenepyrrolidine)-benzoyl], NH-[m-$CH_2$-(1,2,3,4-tetrahydroisoquinoline)-benzoly] NHCO$CH_2$-isoindoline, NH-2-carboxybenzoyl, and NHCO$CH_2$CH(OTBDMS)—$CH_2$COOH.

17. The method of claim 8, wherein the compound has the formula:

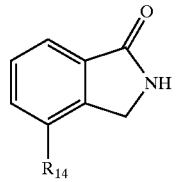

or a pharmaceutically acceptable base or acid addition salt, hydrate, stereoisomer, or mixture thereof, wherein:

$R_{14}$ is hydrogen, halogen, nitro, $NH_2$, hydroxy, —$OCH_3$, —$CH_2NH_2$ or —Q—B—D;

Q is NHCO, NHCONH, O, OCO, NH, $CH_2$ or NHCO—$C_1$–$C_8$ straight or branched chain alkylene;

B is $C_1$–$C_8$ straight or branched chain alkylene, CH=CH, cyclohexyl, phenyl, $C_1$–$C_2$ straight or branched chain alkyl-NH, NH, phenylene, phenyl-$CH_2$, phenyl-NHCO, O—$CH_2$, —CO—, —$CO_2$—, —CONH—, —C(O)—C(O)—, —CONH$CH_2$—, —NHCO— or —$(CF_2)_3$—;

D is hydrogen, halogen, hydroxy, cyclohexyl, $C_1$–$C_{10}$ straight or branched chain alkyl, —$C_1$–$C_4$ straight or branched chain alkyl-$N(R^{18})_2$, —$N(R^{18})_2$, —CH=CHCOO$R^{19}$, —NHC(=NH)$NH_2$, —NHC(=NH)N—COO-t-butyl, —COO$R^{19}$, —NHCO$R^{19}$, —CONH$R^{18}$, phenyl, piperidinyl, anilinyl, piperazinyl, pyrolyl, imidazolyl, benzimidazolyl, tetrazolyl, indolyl, isoquinolinyl, quinolinyl, pyrrolidinyl, purinyl, pyrimidinyl, morpholinyl, thiophenyl, furanyl, isoindolinyl, pyridinyl, prolinyl or nipecotyl, with the proviso that when Q is $CH_2$ and B is a bond or $C_1$–$C_8$ straight or branched chain alkylene, D is not hydrogen or $C_1$–$C_{10}$ straight or branched chain alkyl;

$R^{18}$ is —H, methyl, ethyl, benzyl, cyclohexyl, —COO-t-butyl, $C_1$–$C_2$ alkylene-piperidinyl, $C_1$–$C_2$ alkylene-pyridinyl or $C_1$–$C_2$ alkylene-benzimidazolyl; and $R^{19}$ is hydrogen, methyl, ethyl or —CH(NH-cyclohexyl)$_2$;

wherein each alkyl, alkylene, phenyl, phenylene, piperidinyl, purinyl, isoquinolinyl, indolyl or imidazolyl group is independently unsubstituted or substituted with one or more of the following groups: -halogen, methyl, ethyl, —OCH$_3$, —COOH, —COOCH$_3$, nitro, —N(CH$_3$)$_2$, —CH$_2$-halo, —NHCOCH$_2$-halo, NHCOCH$_2$—N(CH$_3$)$_2$, —O—Si(CH$_3$)$_2$(t-butyl), —O—CH$_3$, —OC(O)CH$_3$, —COO-t-butyl or —CH$_2$—NH—COO-t-butyl.

18. The method of claim 17, wherein $R^{14}$ is selected from the group consisting of H, F, NH$_2$, NO$_2$, NHCOCH$_2$Cl, NHCOCH$_2$N(CH$_3$)$_2$, NHCOCH$_2$N(CH$_2$CH$_3$)$_2$, NHCOCH$_2$N(CH$_3$)-piperazine, NHCOCH$_2$CH$_2$CH$_2$N(CH$_3$)-piperazine, NHCOCH$_2$NH(CH$_2$CH$_3$), NHCOCH$_2$-piperidine, NHCOCH$_2$-1,2,3,4-tetrahydroisoquinoline, NHCOCH$_2$N(CH$_3$)CH$_2$Ph, NHCOCH$_2$(S)-prolinol, NHCOCH$_2$-9-adenine, NHCOCH$_2$-9-(6-chloropurine), NHCOCH$_2$-9-(6-N,N-dimethylpurine), NHCOCH$_2$-benzimidazole, NHCOCH$_2$-ethylnipecotate, NHCOCH$_2$-morpholine, NHCOCH$_2$-pyrrolidine, NHCOCH$_2$-1,2,3,4-tetrahydro-6,7-dimethoxyisoquinoline, NHCOCH$_2$-4-indolemethylester, NHCO-m-NO$_2$-benzoyl, NHCOCH$_2$CH$_2$COOC(NH-cyclohexyl)$_2$, OH, OCH$_3$, OCH$_2$COOCH$_3$, OCH$_2$COOH, OCH$_2$CO-1,2,3,4-tetrahydroisoquinoline, OCO-m-NO$_2$-benzoyl, CH$_2$NH$_2$, CH$_2$NHCO-m-NO$_2$-benzoyl, NHCOCH$_2$CH$_2$CH$_2$COOH, NHCOCH=CHCOOH, NHCOCH$_2$CH$_2$CO-1,2,3,4-tetrahydroisoquinoline, NHCOCH$_2$CH$_2$CH$_2$CO-1,2,3,4-tetrahydroisoquinoline, NHCOCH$_2$CH$_2$OH, NHCOCH$_2$CH$_2$CH$_2$OH, NHCONH-cyclohexyl, NHCO(CH$_2$)$_4$NHtBOC, NHCOCH$_2$CH$_2$CH$_2$CH$_2$NH$_2$, NHCOCHNHtBoc(CH$_2$)$_3$—NH—C=NHN'Boc), NHCOCHNH$_2$(CH$_2$)$_3$-guanidine, NHCOCHNH'Boc(5-CH$_2$—N-tBoc-imidazole), NHCOCHNH'Boc(3-CH$_2$-indole), NH-prolinyl, NH-nipecotyl, NH-3,4,5-trimethoxybenzoyl, NHCOCH$_2$CH$_2$CONH(2-CH$_2$-benzimidazole), NHCO(CH$_2$)$_2$CONH(CH$_2$)$_2$-piperidine, NHCO(CH$_2$)$_2$CONH(CH$_2$)$_2$-piperidine, NHCO(CH$_2$)$_2$CONH(CH$_2$)$_2$-2-pyridine, NHCOCH(NHCOOC$_7$H$_7$)(CH$_2$)$_4$NHtBOc, NHCOCH(NHCOOC$_7$H$_7$)(CH$_2$)$_4$NH$_2$, NHCOCH$_2$COOH, NHCO(CH$_2$)$_2$COOH, NHCO(CH$_2$)$_3$COOH, NHCO(CH$_2$)$_3$COOH, NHCO(CH$_2$)$_4$COOH, NHCO(CH$_2$)$_5$COOH, NHCO(CH$_2$)$_6$COOH, NHCO(CH$_2$)$_7$COOH, NHCO(CH$_2$)$_8$COOH, NHCO(CHOAc)$_2$COOH, NHCO(CF$_2$)$_3$COOH, NHCONHCH$_2$COOH, NHCOCH$_2$OCH$_2$COOH, NHCOCH$_2$NH$_2$, NHCOCH$_2$CH$_2$NH$_2$, NHCOCH(CH$_3$)NH$_2$, NHCOCH$_2$NHCH$_3$, NHCOCH$_2$CH$_2$NHCH$_3$, NHCOCH$_2$tBOC-piperazine, NHCOCH$_2$-piperazine-HCl, NHCO(CH$_2$)$_7$NHCH$_3$, NHCOCH$_2$CO-piperazine-HCl, NHCOCH$_2$CH$_2$Cl, NHCOCH$_2$CH$_2$CH$_2$Cl, NHCOC$_6$H$_4$COCH=CHCOOH, NHCO(2,5-difluorophenyl)COOH, NHCOCH$_2$COOCH$_3$, NHCO(CH$_2$)$_2$COOCH$_2$CH$_3$, NHCOCOCOOCH$_3$, NHCO(CH$_2$)$_4$COOCH$_3$, NHCO(CH$_2$)CH$_3$, NHCO(CH$_2$)$_6$COOCH$_3$, NHCO(p-C$_6$H$_4$—CH=CHCOOCH$_2$CH$_3$), NHCO(CH$_2$)$_8$COOCH$_3$, NH(2-thiophenoyl), NH(2-furoyl), NH(m-chloromethylenebenzoyl), NH(m-N,N-diethylmethylenebenzoyl), NH(m-NHCOCH$_2$Cl-benzoyl), NH(m-NHCOCH$_2$N(CH$_2$CH$_3$)$_2$-benzoyl), NH(m-NHCOCH$_2$N(CH$_3$)$_2$-benzoyl), NH-[m-CH$_2$-(2-hydroxymethylenepyrrolidine)-benzoyl], NH-[m-CH$_2$-(1,2,3,4-tetrahydroisoquinoline)-benzoly] NHCOCH$_2$-isoindoline, NH-2-carboxybenzoyl, and NHCOCH$_2$CH(OTBDMS)—CH$_2$COOH.

* * * * *

UNITED STATES PATENT AND TRADEMARK OFFICE
CERTIFICATE OF CORRECTION

PATENT NO.    : 6,534,651 B2
DATED         : March 18, 2003
INVENTOR(S)   : Jagtap et al.

It is certified that error appears in the above-identified patent and that said Letters Patent is hereby corrected as shown below:

Column 41,
Lines 37-39, thereof, please replace "NH-[m-$CH_2$-(1,2,3,4-tetrahydroisoquinoline)-benzoly] $NHCOCH_2$-isoindoline" with -- NH-[m-$CH_2$-(1,2,3,4-tetrahydroisoquinoline)-benzoyl], $NHCOCH_2$-isoindoline --;
Line 66, thereof, please delete the extra comma after "-O-aryl";

Column 42,
Line 36, thereof, please replace "amine or" with -- or amine --;

Column 43,
Line 46, thereof, please delete the extra comma after "-O-aryl";

Column 44,
Line 14, thereof, please replace "amine or" with -- or amine --;

Column 46,
Lines 24-26, thereof, please replace "NH-[m-$CH_2$-(1,2,3,4-tetrahydroisoquinoline)-benzoly] $NHCOCH_2$-isoindoline" with -- NH-[m-$CH_2$-(1,2,3,4-tetrahydroisoquinoline)-benzoyl], $NHCOCH_2$-isoindoline --;

Column 48,
Lines 29-31, thereof, please replace "NH-[m-$CH_2$-(1,2,3,4-tetrahydroisoquinoline)-benzoly] $NHCOCH_2$-isoindoline" with -- NH-[m-$CH_2$-(1,2,3,4-tetrahydroisoquinoline)-benzoyl], $NHCOCH_2$-isoindoline --.

Signed and Sealed this

Twenty-third Day of September, 2003

JAMES E. ROGAN
*Director of the United States Patent and Trademark Office*